US008603772B2

(12) United States Patent
Debreczeny et al.

(10) Patent No.: US 8,603,772 B2
(45) Date of Patent: Dec. 10, 2013

(54) PARTICLE SENSOR WITH WIDE LINEAR RANGE

(75) Inventors: Martin P. Debreczeny, Danville, CA (US); Jaime Romero, San Leandro, CA (US); Ethan Petersen, Alameda, CA (US)

(73) Assignee: Bug Lab LLC, Concord, CA (US)

( * ) Notice: Subject to any disclaimer, the term of this patent is extended or adjusted under 35 U.S.C. 154(b) by 1252 days.

(21) Appl. No.: 12/220,897

(22) Filed: Jul. 28, 2008

(65) Prior Publication Data

US 2009/0075248 A1    Mar. 19, 2009

Related U.S. Application Data

(60) Provisional application No. 60/962,350, filed on Jul. 28, 2007.

(51) Int. Cl.

| | | |
|---|---|---|
| *C12Q 1/00* | (2006.01) | |
| *C12Q 1/06* | (2006.01) | |
| *G01J 3/12* | (2006.01) | |
| *G01J 3/14* | (2006.01) | |
| *G01J 3/46* | (2006.01) | |
| *G01J 3/50* | (2006.01) | |
| *G01N 21/25* | (2006.01) | |
| *G01N 21/31* | (2006.01) | |
| *G01N 21/85* | (2006.01) | |
| *G01J 3/28* | (2006.01) | |
| *G01J 3/30* | (2006.01) | |
| *G01J 3/32* | (2006.01) | |
| *G01J 3/36* | (2006.01) | |
| *G01J 3/52* | (2006.01) | |
| *G01N 21/27* | (2006.01) | |
| *G01N 21/29* | (2006.01) | |

(52) U.S. Cl.
USPC .............. 435/39; 435/3; 356/330; 356/331; 356/332; 356/333; 356/334; 356/402; 356/403; 356/404; 356/405; 356/406; 356/407; 356/408; 356/409; 356/410; 356/411; 356/412; 356/413; 356/414; 356/415; 356/416; 356/417; 356/418; 356/419; 356/420; 356/421; 356/422; 356/423; 356/424; 356/425

(58) Field of Classification Search
USPC ........ 435/3, 39; 356/330, 331, 332, 333, 334, 356/402, 403, 404, 405, 406, 407, 408, 409, 356/410, 411, 412, 413, 414, 415, 416, 417, 356/418, 419, 420, 421, 422, 423, 424, 425
See application file for complete search history.

(56) References Cited

U.S. PATENT DOCUMENTS

| | | |
|---|---|---|
| 3,420,609 A | 1/1969 | Kozawa |
| 3,518,437 A | 6/1970 | Riggs |
| 4,160,914 A | 7/1979 | Wynn |
| 4,193,692 A | 3/1980 | Wynn |
| 4,420,256 A | 12/1983 | Fladda et al. |
| 4,451,152 A | 5/1984 | Topol et al. |
| 4,492,462 A | 1/1985 | Pross et al. |
| 4,641,969 A | 2/1987 | Lundberg et al. |
| 4,783,599 A | 11/1988 | Borden |
| 4,786,171 A | 11/1988 | LeFebre et al. |
| 5,168,367 A | 12/1992 | O'Rourke |
| 5,185,531 A | 2/1993 | Wynn |
| 5,268,736 A | 12/1993 | Prather |
| 5,371,016 A | 12/1994 | Berndt |
| 5,427,920 A | 6/1995 | Berndt et al. |
| 5,454,016 A | 9/1995 | Holmes |
| 5,457,526 A | 10/1995 | Kosaka |
| 5,483,080 A | 1/1996 | Tam |
| 5,602,647 A | 2/1997 | Xu et al. |

(Continued)

FOREIGN PATENT DOCUMENTS

| | | |
|---|---|---|
| JP | 04-273065 A | 9/1992 |
| WO | WO 8002876 A1 * 12/1980 ............ G01N 15/02 |  |

OTHER PUBLICATIONS

Tissue, Brian M. 2000. CHP—Beer-Lambert Law, pp. 1-5. http://www.files.chem.vt.edu/chem-ed/spec/beerslaw .html, Printed Nov. 1, 2012.*

(Continued)

*Primary Examiner* — Jon P Weber
*Assistant Examiner* — Kailash C Srivastava
(74) *Attorney, Agent, or Firm* — Paul Littlepage; Gary Baker; Quine Intellectual Property Law Group, P.C.

(57) ABSTRACT

This invention provides a novel methods and devices for measurement of particle concentration or changes in particle concentration over a wide linear range. The invention comprises one or more radiation sources and one or more detectors contained in a housing which is interfaced to a medium containing particulate matter. The one or more radiation sources are directed into the medium, scattered or transmitted by the particulate matter, and then some portion of the radiation is detected by the one or more detectors. Methods for confining the measurement to a specific volume within the medium are described. Algorithms are provided for combining the signals generated by multiple source-detector pairs in a manner that results in a wide linear range of response to changes in particle concentration. In one embodiment the sensor provides non-invasive measurements of biomass in a bioreactor. In another embodiment an immersible probe design is described, which may be suited for one-time use. In an addition embodiment, a sensor is provided which is well suited to the rapid sequential measurement of particle concentration in multiple vessels, such as assessment of biomass in series of shake flasks.

47 Claims, 18 Drawing Sheets

(56) References Cited

U.S. PATENT DOCUMENTS

| | | |
|---|---|---|
| 5,773,828 A | 6/1998 | Akiyama et al. |
| 5,818,583 A | 10/1998 | Sevick-Muraca |
| 5,831,721 A | 11/1998 | Alkafeef |
| 5,876,674 A | 3/1999 | Dosoretz et al. |
| 5,905,271 A | 5/1999 | Wynn |
| 6,456,375 B1 | 9/2002 | Ottens et al. |
| 6,567,166 B2 | 5/2003 | Ottens et al. |
| 6,573,991 B1 | 6/2003 | Debreczeny et al. |
| 6,643,016 B2 | 11/2003 | Garver et al. |
| 6,683,314 B2 | 1/2004 | Oostman, Jr. et al. |
| 6,760,107 B1 | 7/2004 | Drake |
| 7,054,002 B1 | 5/2006 | Sevick-Muraca et al. |
| 7,100,462 B2 | 9/2006 | Gronvall |
| 7,164,477 B2 | 1/2007 | Yokota |
| 7,187,441 B1 | 3/2007 | Sevick-Muraca et al. |
| 7,557,923 B2 * | 7/2009 | Lodder .................. 356/407 |
| 2005/0264817 A1 | 12/2005 | Havard et al. |

OTHER PUBLICATIONS

Agilent Technologies. 1993. 8452 UV-Vis Spectrophotometers Brochure, pp. 1-2.*

Olis (undated). Ohs® HP 8452 Diode Array A Comprehensive Upgrade to a Trusted Spectrometer, pp. 1-8, Printed Nov. 4, 2012.*

* cited by examiner

PARTICLE SENSOR WITH WIDE LINEAR RANGE

CROSS-REFERENCE TO RELATED APPLICATIONS

This application is related to, and claims benefit of, U.S. Provisional Patent Application Ser. No. 60/962,350 filed Jul. 28, 2007, the disclosure of which is incorporated herein by reference in its entirety for all purposes.

FIELD OF INVENTION

The present invention relates generally to methods and devices for determining particle concentration in a medium through use of radiation sensors and detectors and algorithms to extend the linear range between particle concentration and radiation attenuation. Specific embodiments of the invention relate to biomass and growth rate monitoring using optical scattering or transmission to measure the concentration or rate of change of growth of cells or microorganisms in liquid cultures.

BACKGROUND

Radiation Sensors for the Measurement of Particle Concentration

In various media the dynamic range of particle concentration that can be measured by typical radiation sensors is limited by the non-linear relationship between the concentration of particles and attenuation of the radiation used (e.g., light). For different concentrations of absorbing or scattering particles in a medium, the light level impinging upon a sensor will vary widely. When the concentration of particles in the medium is low enough that the mean distance between particles is large as compared to the distance between a radiation source and a detector, the particles will have little measurable effect on the detected radiation. On the other hand, when the mean distance between particles is small compared to the distance between the source and detector, the effect of adding more particles will be non-additive due to multiple scattering and the screening effect of particles aligned along the same radiation path. For these reasons, sensors that measure the transmission or reflectance of radiation through a single fixed path length of material (e.g., through a medium comprising particles to be measured) have an inherently narrow linear range over which material particle concentration can be accurately measured.

Past attempts to overcome this linearity limitation have included ratiometric combining of transmission and reflectance measurements, as for example described in U.S. Pat. No. 4,193,692 to Wynn. However, even in such attempts the range of linearity that is achieved is still too limited for many applications. Furthermore, the optical arrangement required to measure both transmission and reflectance would make it difficult or impossible to conduct measurements non-invasively in many applications.

Measurement of Biomass in Liquid Cultures

A particularly important area in which determination of particle concentration arises is in measurement of cell biomass in liquid culture. Liquid cultures of cells (e.g., microorganisms) are frequently grown for research purposes or for commercial use. For example, cells can be genetically modified to produce high yields of chemicals that would otherwise be difficult, expensive, or impossible to synthesize.

In order to prevent growth of undesirable cells or contaminants, it is important that the culture be grown under sterile conditions. For this reason, the growth medium is sterilized prior to inoculation with the desired cell. Furthermore, in order to maintain a barrier to foreign organisms entering the sterilized medium and also to optimize the growth of the desired cell, liquid cultures are frequently grown under highly controlled conditions in fermentors or bioreactors. In addition to maintaining sterile conditions, bioreactors can provide control over such parameters as temperature, pH, rate of stirring, and concentration of nutrients and dissolved gases.

Cells in such bioreactors (and in other media containments) typically undergo several stages of growth in the medium. After inoculation, the initial growth rate of the cells can be slow, as the organism becomes accustomed to the new environment. This slow growth is frequently followed by a rapid growth phase where the biomass of the cells increases nearly exponentially. This growth period is sometimes referred to as the "log phase" due to the fact that the change in the logarithm of biomass is nearly linear with time. The growth rate or "doubling time" of a cell or organism is useful for predicting the time at which a culture will achieve a desired biomass. Unfortunately, the non-linear response of currently available sensors to biomass, makes accurate estimation of growth rate difficult or impossible.

As the nutrient supply relative to the biomass diminishes, the growth of cell culture will slow. In order to achieve maximum biomass, it is preferable that the conditions in the bioreactor change during the different phases of growth. Ideally a feedback mechanism would link the measured growth of the cells or microorganisms to the conditions in the bioreactor. Furthermore, a physical or chemical stimulus can be used to induce production of a desired chemical by the cells or microorganisms. The timing of this induction relative to the growth cycle of the cells or microorganisms can be often critical in order to achieve maximum chemical yield. Unfortunately, methods of continuously and reliably measuring the growth of cells or microorganisms in liquid cultures are not very robust, especially over a wide range of concentrations.

The most commonly used method of measuring the biomass in cultures is to extract a portion of the liquid and measure its optical density in a spectrophotometer. This method has several disadvantages: (1) each time liquid is withdrawn, there is a risk that the culture will be contaminated, (2) the method is not continuous, and (3) the method is labor intensive, requiring frequent extraction and precise volumetric dilution of the extracted liquid (especially when high cell concentrations are measured). Some current commercial devices offer continuous measurement of optical density using a probe that is immersed in the liquid culture. Unfortunately, such devices are prone to drift, particularly due to growth of cells or microorganisms on the sensor itself. In addition, the range of biomass that can be measured is severely limited by the use of fixed path length transmission or reflectance measurements. Many microorganisms, particularly strains of yeast (e.g., *Pichia Pastoris*), are grown to much higher concentrations (e.g., 50 g/L and higher) than can be reliably measured with any known commercially available device based on optical transmittance.

In general, prior attempts to non-invasively measure biomass have been limited by the linear range of response between a measured signal (e.g., light transmission through the culture) and concentration/biomass of the culture, or by sensitivity to vessel wall thickness. For example, U.S. Pat. No. 5,483,080 to Tam describes a non-invasive method for measuring biomass in liquid cultures using optical reflectance. However, the sensor response is highly non-linear with changes in concentration of cells. In addition, a specific calibration would need to be provided for each type of vessel on which the method is practiced, due to the sensitivity of the method to variable glass thickness.

Thus, there is a continuing need for improved methods and devices for accurately measuring particle concentration of various types of particles over a range of concentrations. The invention described herein fulfills these and other needs as will be apparent upon review of the following.

SUMMARY OF INVENTION

In various aspects, the current invention comprises a radiation sensor device for measuring particle concentration or changes in particle concentration over a wide linear range. In various embodiments, the sensor comprises of one or more radiation sources and one or more detectors contained in a housing. The sensor can be interfaced to a medium containing particulate matter. The one or more radiation sources are directed into the medium, scattered by the particulate matter, and then some portion of the radiation is detected by the one or more detectors (e.g., radiation reflected back from the medium or transmitted through the medium). Embodiments of the invention also include methods for confining the measurement to a specific volume within the medium are described as well as algorithms for combining the signals generated by multiple source-detector pairs in a manner that results in a wide linear range of response to changes in particle concentration.

In one embodiment, the sensor comprises a near-infrared laser light source and four detectors. In such embodiment, the sensor is mounted to the exterior of a vessel, such as a bioreactor, containing cells or microorganisms. Laser light is directed through a window in the vessel into the medium and is scattered by the cells or microorganisms. Three of the detectors are arranged to collect the scattered light through three different paths through the medium. Each detector is placed at the end of a long, narrow aperture made of a material that is strongly absorptive of the laser light. The detector aperture spaced farthest from the source includes a mirror that allows the sensor to be more compact. The signals from the three paths are combined to produce a single output which has linear response to the biomass concentration in the vessel over a wide range of biomass. The sensor geometry is arranged so that substantially only particles confined to a particular volume of the vessel contribute to the detected signal. The fourth detector is used to directly measure the output of the laser, providing a signal used to compensate for intensity variation such as may be caused by temperature fluctuations. The sensor can be surrounded by a shell that includes stackable support elements. By the removal or addition of the stackable elements, windows with apertures that are variably recessed can optionally be accommodated. Sensor calibration during manufacturing can be achieved through the use of a series of variably reflective materials. Similarly, subsequent to manufacture the sensor performance can be checked and re-calibrated through the use of at least one reflective material. In one embodiment, these materials can include acrylic with variable amounts of diffusant embedded in the matrix.

In yet other embodiments of the invention, the sensor is designed to be manually placed in close proximity to a vessel, such as a shake flask. A rapid measurement of particle concentration can be activated by contact with the vessel. In such manner, many vessels can be measured in rapid succession. Methods for ensuring alignment of the sensor optics relative to the vessel are provided. Further, methods for reducing sensitivity to thickness of the container wall are also provided.

In yet another embodiments, the invention comprises a probe designed to be immersed in the medium of interest. The invention includes probe designs compatible with narrow immersion ports, such as may be commonly found in bioreactors. The invention also includes an inexpensive probe suited for single use, which could be used in conjunction with a disposable bioreactor.

These and other features of the invention will become more fully apparent when the following detailed description is read in conjunction with the accompanying figures and claims.

DETAILED DESCRIPTION OF THE INVENTION

Figure 1:
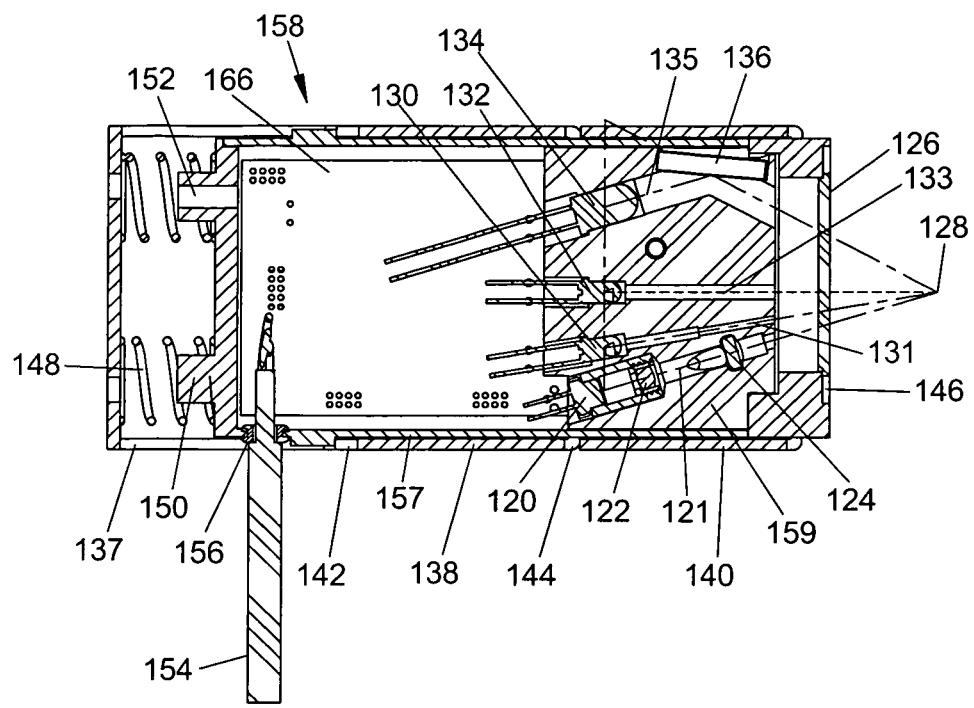
FIG. 1 depicts an exemplary cross-sectional view of a sensor of the present invention designed for mounting to the exterior of a vessel.

The present invention comprises various methods, systems, and devices to more accurately determine particle concentration in a medium. The invention is useful in numerous settings, including, e.g., monitoring of cell culture growth, determination of cell culture biomass, etc. However, it will be appreciated that while the invention is primarily discussed herein in terms of its use with cell culture, it is also capable of use with myriad other applications where accurate determination of particle concentration is desired. Furthermore, while the devices and systems herein are primarily presented in particular configurations, those of skill in the art will appreciate that the invention also includes other configurations (e.g., those having a different number of radiation sources and/or radiation detectors than those used as illustrations herein). Thus, even though in certain embodiments, the invention is directed towards particular configurations and/or combinations of aspects (e.g., radiation sources, arrangement of the radiation sources and detectors in relation to one another, etc.), those of skill in the art will appreciate that not all embodiments necessarily comprise all aspects or particular configurations unless specifically stated to do so.

In brief, the invention comprises devices having at least two radiation source/detection pairs (e.g., a single source paired with a first detector and also paired with a second detector), which transmit radiation (e.g., light) through a medium (e.g., a liquid cell culture) and measure the reflected and/or transmitted radiation. The different source/detector pairs in the devices have different separations (distances between the source and the detector) which causes the radiation measured at one detector to have traveled a different path than the radiation at a second detector. Through use of algorithms, the methods of the invention allow the determination of concentration over a wide linear (and thus more accurate) range, e.g., by choosing to use the signal from a particular source/detector pair at a particular particle concentration or by combining the signals from particular source/detector pairs at a particular concentration.

The methods and devices of the invention provide numerous benefits. For example, but not limited to, the following, various embodiments of the invention are beneficial in that: the combined sensor response of the invention has a wide linear range of sensitivity to changes in a function (e.g., radiation attenuation) dependent on particle concentration; the sensor response has low sensitivity to objects outside of a selected measurement region; the use of folding mirrors within some embodiments of the invention helps reduce the size of the sensor; the sensor has low sensitivity to changes in ambient lighting conditions; the sensor is easily and rapidly calibrated during manufacturing; the sensor calibration is easily and rapidly checked and adjusted by the user; the rate of change of particle concentration can be rapidly and accurately determined; and the sensor response has low sensitivity to changes in temperature.

Additionally, in embodiments of the invention that comprise a sensor that is mounted externally to a container holding a liquid culture to be monitored (e.g., for the purpose of measuring the biomass), various embodiments of the invention provide benefits that include, but are not limited to: elimination of the need to sterilize the sensor and its housing; the sensor housing can be constructed for lower cost than sensor housings requiring sterilization and immersion in a liquid culture; the risk of contaminating the liquid culture with foreign matter is eliminated or greatly reduced; multiple different containers can be monitored with the same sensor without interrupting the growth of the cultures or risking exposure of the cultures to foreign matter or causing cross contamination between cultures; the measured value of biomass in a liquid culture is compensated for variations in window thickness between different containers; the sensor can be stably mounted to a wide variety of different container types; the measurement is completed rapidly; multiple vessels may be sequentially measured; the user can be prevented from taking a reading until the sensor is properly placed relative to the container; measurement values can be read directly from the sensor or stored internally for later use; and the growth rate of the culture can be rapidly and accurately estimated.

Again, while described primarily herein in terms of monitoring of cell culture or microbial growth and the like, the methods and instruments of the present invention can also be used to determine concentration of particles in liquid suspensions and solids other than for determination of biomass. For example, the particulate content in milk, the rate of polymerization in a chemical system or the turbidity of water can be measured by application of the methods and/or instruments of the present invention. Similarly, the present invention can be utilized to determine the amount of gas in a liquid phase, such as the concentration of gas bubbles in a liquid medium, or the concentration of liquid droplets in a gaseous medium. In addition, the attenuation of radiation by absorption can be used to measure the concentration of components dissolved in solution, by application of the present invention.

The method and instruments of the present invention can also be useable for determination of concentration of particles in gas phase. For example, in industrial plants using smokestacks, the amount or concentration of a specific component of the effluent gas can be measured through use of the present invention. As another example, the invention can be used to measure the particulate content of a gas for the purpose of smoke or fire detection. As yet another example, the invention can be used to measure the concentration of a particular component of a gas, such as the concentration of carbon dioxide in a mixture of gases or the density of fog or smoke in the flight path of an airplane.

In addition, the methods and/or instruments of the present invention can be utilized to monitor materials in the solid state and to monitor transformation of materials between states. For example, the invention can be used to measure the concentrations of oxygenated and deoxygenated hemoglobin in tissue. As another example, the invention can used to monitor the conversion of a liquid to the solid state, such as gel formation. Again, although the description herein primarily refers to the measurement of the biomass in a liquid culture, it will be appreciated that the methods and instruments of the invention are also applicable in other liquids and in gas and solid media applications.

Definitions

Before describing the present invention in detail, it is to be understood that the invention herein is not limited to use with particular particle types or radiation sources, which can, of course, vary. It is also to be understood that the terminology used herein is for the purpose of describing particular embodiments only, and is not intended to be limiting. As used in this specification and the appended claims, the singular forms "a," "an," and "the" include plural referents unless the context clearly dictates otherwise. Thus, for example, reference to "a radiation source" optionally includes a combination of two or more radiation sources, and the like.

The terms "particle" and "particulate," as used herein, refer to both soluble (dissolved) and insoluble matter in liquid solutions or present within solids. Particles include airborne matter and can include matter ranging in size from single molecules up to matter that is visible to the naked eye. Examples of such particles can include cells (e.g., eukaryotic or prokaryotic cells, etc.) present in liquid media, dust or other fine particles suspended in air, water droplets suspended in air, fats or proteins suspended in liquid or gel (either singularly or within groupings such as micelles), and particles suspended in solids. In particular embodiments particles include cells such as microorganisms or eukaryotic cells in liquid culture.

Measurement of cell concentration determines the "biomass" in a liquid culture. The term "biomass" as used herein, refers to the concentration of biological material, such as cells or microorganisms within a sample. Examples of such biological material include, but are not limited to, prokaryotic cells, eukaryotic cells, bacteria such as *Escherichia coli*, yeast such as *Saccharomyces cerevisiae*, fungi, algae, and animal and plant cells.

As used herein, "concentration" refers to the number of a type of particle, weight of a type of particle, or volume of a type of particle found in a given volume of a medium.

The term "radiation" herein, refers to electromagnetic or acoustic energy. Examples can include sound waves, light in the ultraviolet, visible, and infrared ranges, microwaves, and x-rays.

"Optical Density" (OD) is a frequently measured quantity that can, in some circumstances, be related to particulate concentration. OD is defined as:

$$OD = -\log_{10}\left(\frac{I}{I_0}\right) \quad \text{(Equation 1)}$$

where light intensities are measured after transmission through a sample (I) and in the absence of the sample ($I_0$). By diluting a particulate sample to have an OD in a linear range of response (commonly OD<1, but more ideally OD between 0.05 and 0.2) and scaling the measured OD by the dilution factor, a linear relationship between particle concentration and OD may be established for many particle types.

Device and System Overview

The detailed description set forth herein along with the appended drawings is intended merely as a description of various embodiments of the invention, and is not intended to represent the only form in which the invention may be constructed or utilized. The description sets forth the functions and sequence of steps for construction and implementation, etc., of the embodiments of the invention.

Sensor Housing and Interface with Samples

It will be appreciated that the various components herein, e.g., the radiation sources, the radiation detectors, the lenses, etc., are typically arranged on a mounting block, scaffolding, chassis, or framework and optionally are present within a housing to fully or partially enclose the sensor instrument. The particular configuration of such framework and/or housing can optionally vary in different embodiments based upon, e.g., the particular components, their size, etc. The sensor housing can be constructed from various material, e.g., any or all of: metal, resins, plastics, etc. In typical embodiments however, the framework keeps the various components secure and in the proper location and orientation while also optionally aiding in the movement of the components when necessary. The framework can be rigid enough to prevent vibrations within the instrument and the various components. Additional aspects of framework and mounting that aid in tying together the various components and aspects of the device/system include various alignment and mounting couplers, etc.

It will also be appreciated that the materials that comprise the mounting block (or parts thereof or therein) can in some embodiments, be strongly absorbent to radiation. Thus, the long narrow apertures described in some embodiments herein can be of radiation absorbent material. Such apertures can be fabricated by molding or machining the material of the mounting block. The optical components of the devices herein can also be mounted within the mounting block by appropriate shaping of the mounting block at the end of the apertures. In many embodiments, a window is provided at the interface between the sensor and the outside environment, thus, allowing interaction with samples. The window can seal the sensor against contaminants and can allow radiation to pass from the source into the sample and optionally from the sample back into the device to the detectors. In some embodiments the window selectively blocks radiation in certain wavelength ranges (e.g., in order to help reduce ambient light contamination, etc.). A gasket can be used to surround the window to help reduce contamination of the interior of the device. Thus, for example, the gasket can help in preventing contamination of the device interior when the device is placed in contact with a vessel containing a sample.

In various embodiments, the sensor device is present in a system with a base unit. Such base units can comprise, e.g., a digital display, a graphical display, analog and digital signal outputs, and a user interface for changing instrument settings as well as computer or processing aspects. See below. The communication between the sensor aspect and aspects in the base unit can be analog or digital, wired via a cable or other similar connection, or wireless (e.g. infrared or radiofrequency).

Sources and Detectors

In the various embodiments, a laser diode light source and photodiode detector are described. However, many other light sources and detectors can be substituted for the specific illustrations herein without substantially modifying the essential features of the invention. Other radiation (e.g., light) sources that can be used in embodiments of the invention include, e.g., vertical cavity surface emitting lasers (VCSELs), light emitting diodes (LEDs), resonant cavity light emitting diodes, solid state lasers (e.g. Nd—YAG), gas lasers (e.g. HeNe), and white light sources such as light bulbs.

Other radiation sources that can be used in embodiments of the invention can include, e.g., microwave sources, such as magnetrons, klystrons, gyrotrons, traveling wave tubes, and transistors; terahertz radiation sources such as quantum cascade lasers, far infrared laser, gyrotrons, and backward wave oscillators; acoustic sources such as speakers and ultrasound transducers; and x-ray sources such as x-ray tubes.

The detectors in the embodiments of the invention can comprise various photodiodes, CCDs, cameras, etc. Those of skill in the art will be familiar with various detection components and specific examples of such are presented below. Other light detectors that can be used in embodiments of the invention can include, e.g., phototransistors, photovoltaic cells, photomultipliers, and avalanche photodiodes. Other radiation detectors that can be used in embodiments of the invention include semiconductor detectors, photostimulable phosphors, Geiger counters, bolometers, and microphones.

Optical Configurations and Optical Geometry

Figure 12A:
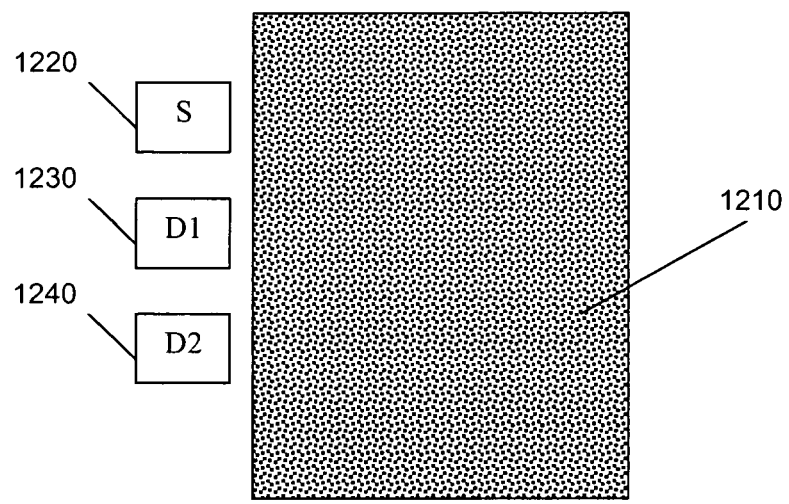
FIG. 12a depicts a diagram of an exemplary reflective optical arrangement of the invention employing one source and two detectors.
Figure 12B:
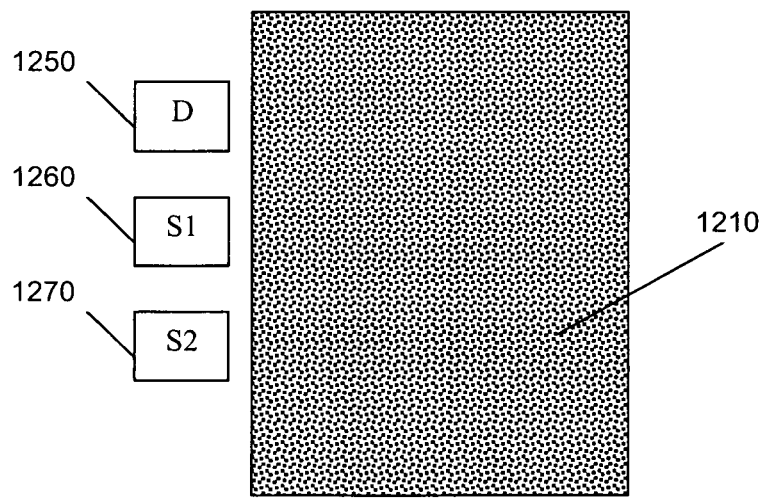
FIG. 12b depicts a diagram of an exemplary reflective optical arrangement of the invention employing two sources and one detector.
Figure 13A:
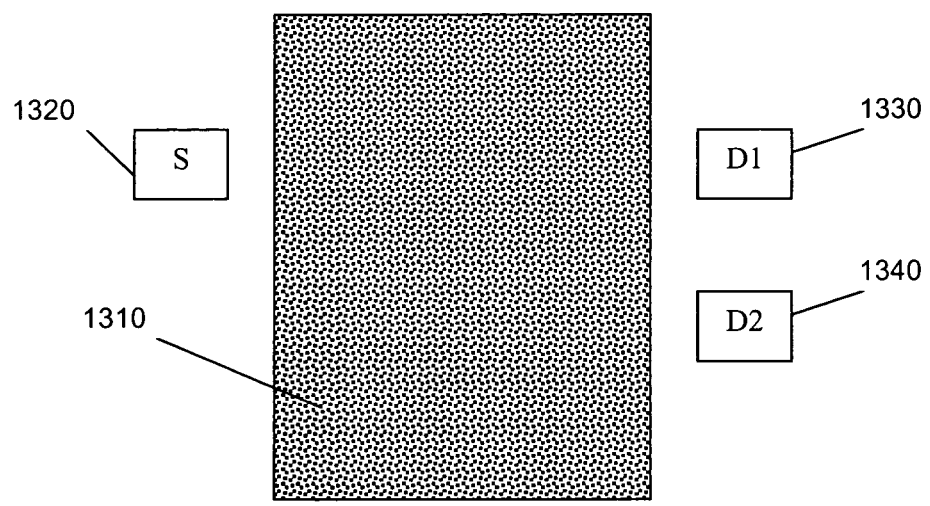
FIG. 13a depicts a diagram of an exemplary transmissive optical arrangement of the invention employing one source and two detectors.
Figure 13B:
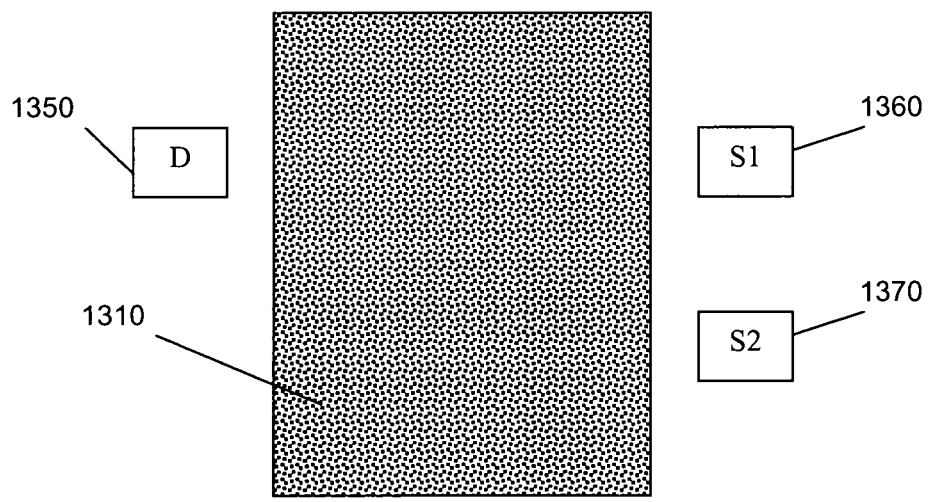
FIG. 13b depicts a diagram of an exemplary transmissive optical arrangement of the invention employing two sources and one detector.
Figure 16A:
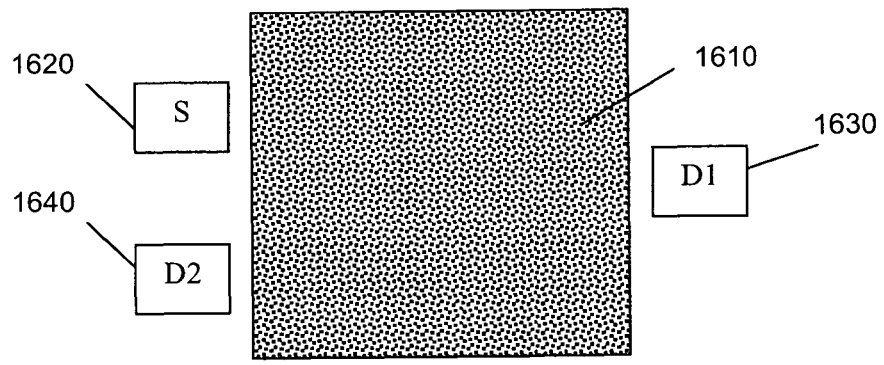
FIG. 16a depicts a diagram of an exemplary combined reflective and transmissive optical arrangement of an embodiment of the invention employing one source and two detectors.
Figure 16B:
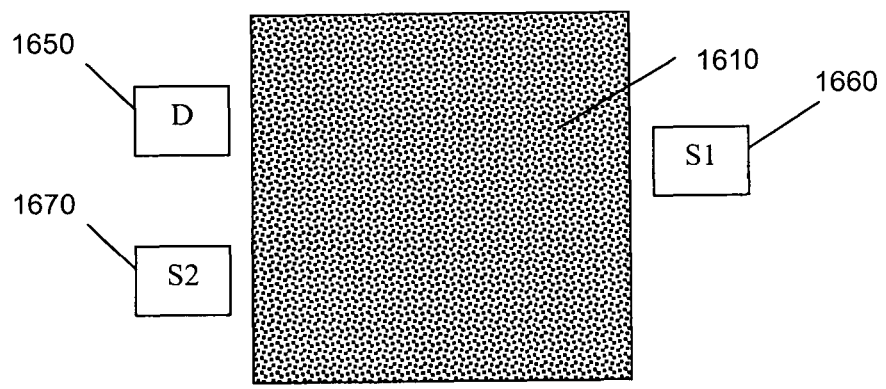
FIG. 16b depicts a diagram of an exemplary combined reflective and transmissive optical arrangement of an embodiment of the invention employing two sources and one detector.

The various radiation sources and detectors can vary between embodiments, not only in number, but also in location/orientation within the sensor and with relation to a sample to be measured. In a very generalized sense, the sources and detectors can be arranged in relation to a sample to be monitored as presented in FIGS. 12, 13, and 16. One exemplary source and detector arrangement that can be employed in the present invention is depicted in FIG. 12a. In FIG. 12a, radiation source 1220 is positioned so that it is directed into medium of interest 1210. Two or more detectors (detectors 1230 and 1240) are positioned to collect reflected radiation after it has interacted with the medium. While in many embodiments, the source and the detector will be present in a single housing, it will be noted that the detectors are positioned at different distances from the radiation source, thus causing the radiation to travel different paths through the medium to reach the detectors. An alternate optical arrangement having two radiation sources (sources 1260 and 1270) and single detector 1250 is depicted in FIG. 12b. As can be seen, the illustrations in FIG. 12 comprises two source/detector pairs even though there are only three components (i.e., S-D1 and S-D2 or D-S1 and D-S2). The embodiments illustrated in FIGS. 12a and 12b are arranged so that radiation scattered from within the medium is detected (i.e., with medium 1310, detectors 1330 and 1340 and source 1320 in FIG. 13a and detector 1350 and sources 1360 and 1370 in FIG. 13b). In alternate embodiments, as depicted in FIGS. 13a and 13b, the source(s) and detector(s) are arranged so that radiation is transmitted through the medium of interest and then detected. In yet other embodiments, the sources and detectors are arranged so that both transmitted and reflected radiation are detected. For example, see, FIG. 16. FIG. 16a shows source 1620 and detectors 1640 and 1630 around medium 1610, while FIG. 16b shows detector 1650 and sources 1670 and 1660 around medium 1610. The optical arrangements depicted in FIGS. 12, 13, and 16 are be readily expanded in other embodiments by adding additional sources or detectors, as required for particular applications.

Figure 9A:
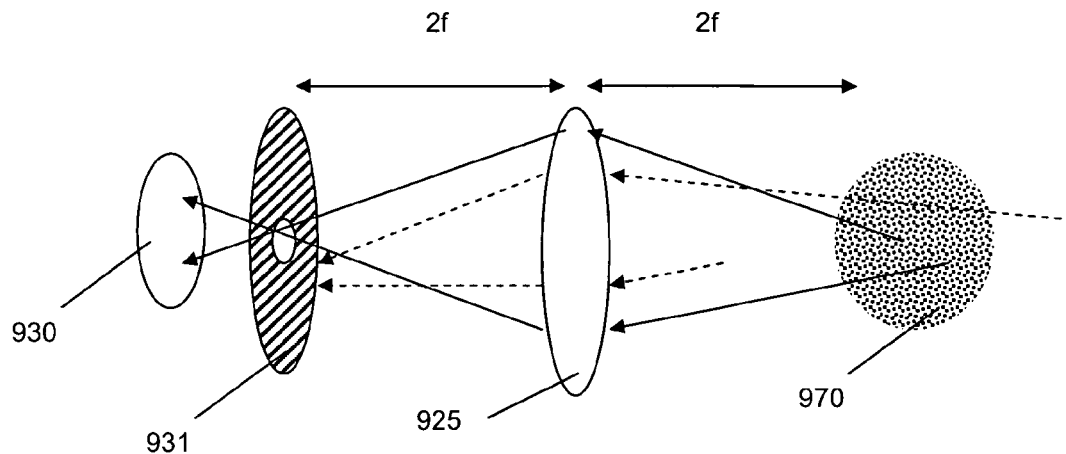
FIG. 9a depicts a diagram of an exemplary optical arrangement of the present invention employing a pin-hole aperture.

In many applications, it can be useful to limit the particle measurement to a well-defined volume within the medium of interest. Exemplary embodiments for accomplishing this are illustrated in FIGS. 9a-e (which share numbering). As can be seen, FIGS. 9a-9e show various aspects of embodiments of the invention in isolation. In FIG. 9a, lens 925 and aperture 931 are positioned in front of radiation detector 930. The lens is positioned so that primarily only radiation emanating from within volume of interest 970 (e.g., within a cell culture) will pass through the aperture. In the figure, the solid lines from the volume of interest can be seen to traverse the lens and pass through the aperture while the dashed lines indicating radiation (e.g., light) from outside of the area of interest do not pass through the aperture. The detector is positioned behind the aperture, so that primarily only radiation passing through the aperture will be detected.

Figure 9B:
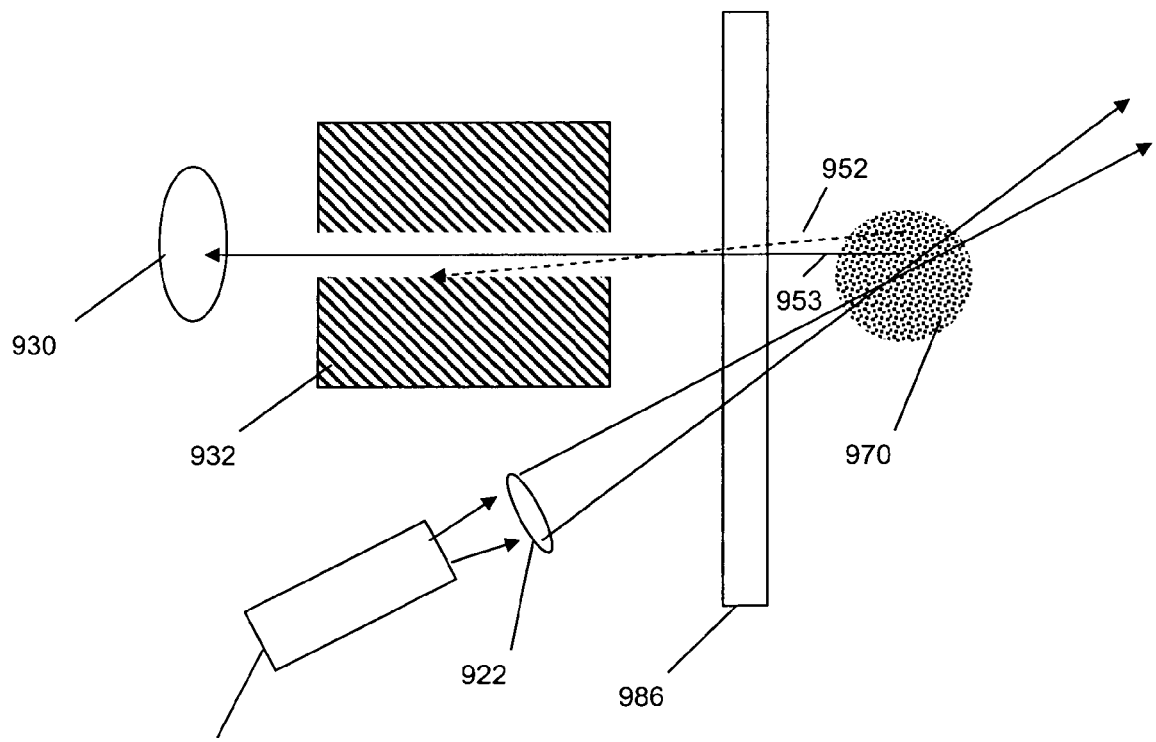
FIG. 9b depicts a diagram of an exemplary reflective optical arrangement of the present invention employing a long aperture and an angled, focused laser.
Figure 9C:
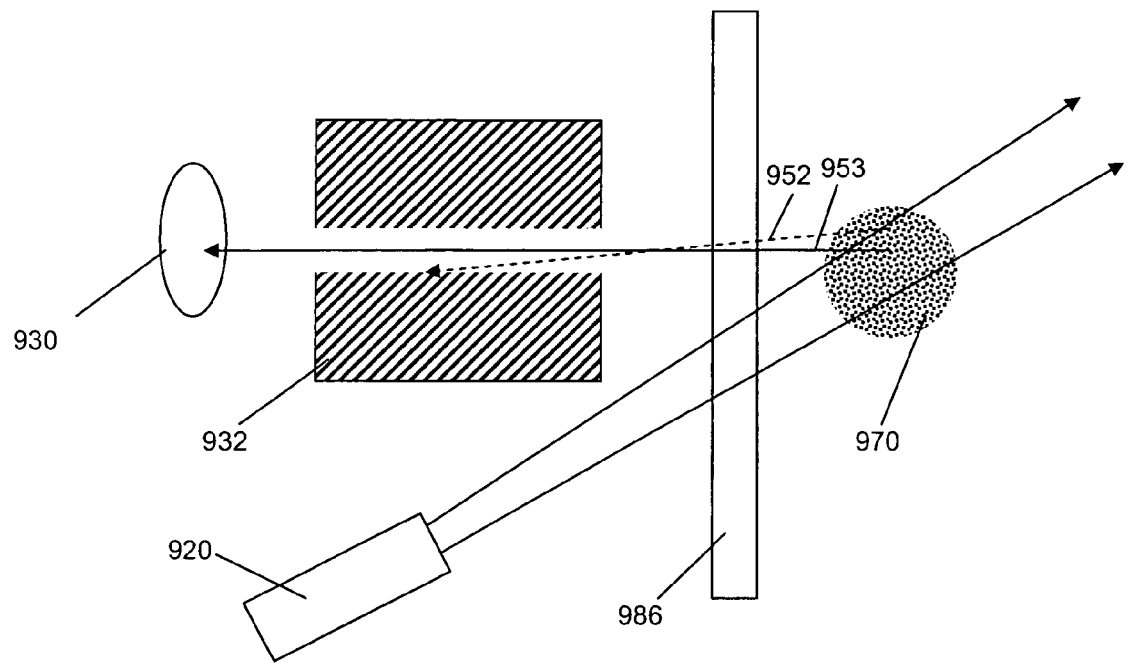
FIG. 9c depicts a diagram of an exemplary reflective optical arrangement of the present invention employing a long aperture and an angled laser.
Figure 9D:
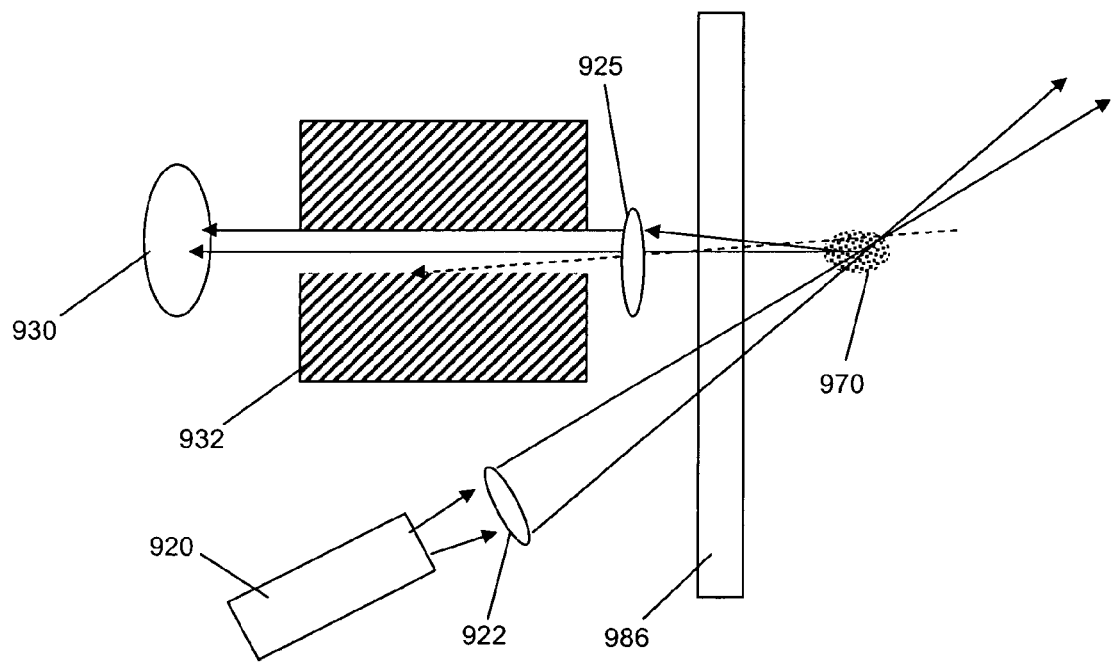
FIG. 9d depicts a diagram of an exemplary reflective optical arrangement of the present invention employing a long aperture with a lens and an angled, focused laser.

FIG. 9C shows another embodiment in which long aperture 932 (which can be comprised of material that is strongly absorbing of radiation emitted by the source), is positioned in front of detector 930. The aperture allows primarily only radiation emanating from within a narrow cone to pass through without being absorbed. Cf. dotted line 952 with solid line 953. The detector is positioned so that primarily only light passing through the aperture is detected. The detector and aperture are positioned relative to radiation source 920 so that the cone of detection and the radiation beam cross at an angle. The zone of overlap between the radiation beam and the detection cone define volume 970 within which radiation will be detected. In other embodiments, e.g., as depicted in FIG. 9b, the radiation source is focused by lens 922. By making the focal point of the radiation coincide with the zone of overlap between the radiation beam and detection cone, the measurement volume is further reduced, and discrimination against radiation emanating from outside of the zone of overlap is enhanced. In another embodiment, e.g., as depicted in FIG. 9d, lens 925 is used in front of the aperture to further define or restrict the measurement volume. Vessel wall 986 is also shown in FIG. 9.

Thus, the geometric arrangement of the sensor components in the various embodiments limits the measurement of the particles to a well-defined volume in a medium by several mechanisms, as illustrated in FIGS. 9a-e. A first mechanism, illustrated in FIGS. 9b-d, comprises angling of the beams from radiation source 920 (e.g., a laser) and to detector 930 so that they overlap maximally within the medium of interest. A second mechanism (as shown in FIGS. 9b, d, and e), comprises focusing the output of the radiation source so that the point of highest radiation intensity substantially coincides with the zone of overlap. A third mechanism (as shown in FIGS. 9*a-e*) uses aperture 931 or aperture 932 to restrict detection of radiation from outside of the zone of overlap. A fourth mechanism (as shown in FIGS. 9*a, d,* and *e*) uses lens 925 in front of an aperture to exclude radiation emanating from outside of the volume of interest from passing though the aperture. A fifth mechanism (as shown in FIGS. 9*b-e*) uses a long narrow aperture optionally constructed from a material that is highly absorptive to the source radiation, to restrict the size of the detection cone.

As will be appreciated, these mechanisms can be combined in various ways according to the needs of the particular application. For example, the embodiment illustrated in FIGS. 1-4 shows combination of the first, second, third, and fifth mechanisms as described above. The three detectors in FIGS. 1-4 are arranged such that the zone of overlap between the radiation source (e.g., a laser) and each detector substantially coincides for all three source-detector pairs. In order to achieve this, the greater the source-detector separation is, the greater the angle formed by the radiation source and detector beams emanating from the point of maximal overlap. Thus, if the aperture diameter for all three detectors were equal, the zone of overlap would greatly increase with decreasing angle between the laser and detection beams. Instead, by reducing the aperture diameter for the closer source-detector pairs, the zone of overlap is kept relatively constant across the three detectors. Thus in some embodiments such as illustrated in FIGS. 1-4 comprising multiple apertures, each aperture can have a different diameter and/or length depending upon, e.g., the angle between the radiation source and the detector.

In general, the size of the sensor can be restricted by the aperture or window available for accessing or viewing the medium. On the other hand, as shown below, the wider the range of source-detector separations employed in the sensor, the wider the range of sensitivity to particle concentration. The sensor design of various embodiments of the present invention overcome these opposing constraints through the use of a folding mirror. As can be seen in FIG. 1, mirror 136 employed in third detector aperture 135 allows the height of the sensor to be reduced by approximately 25% compared to a sensor constructed with the same source-detector separations and aperture lengths, without the use of a mirror.

Figure 14A:
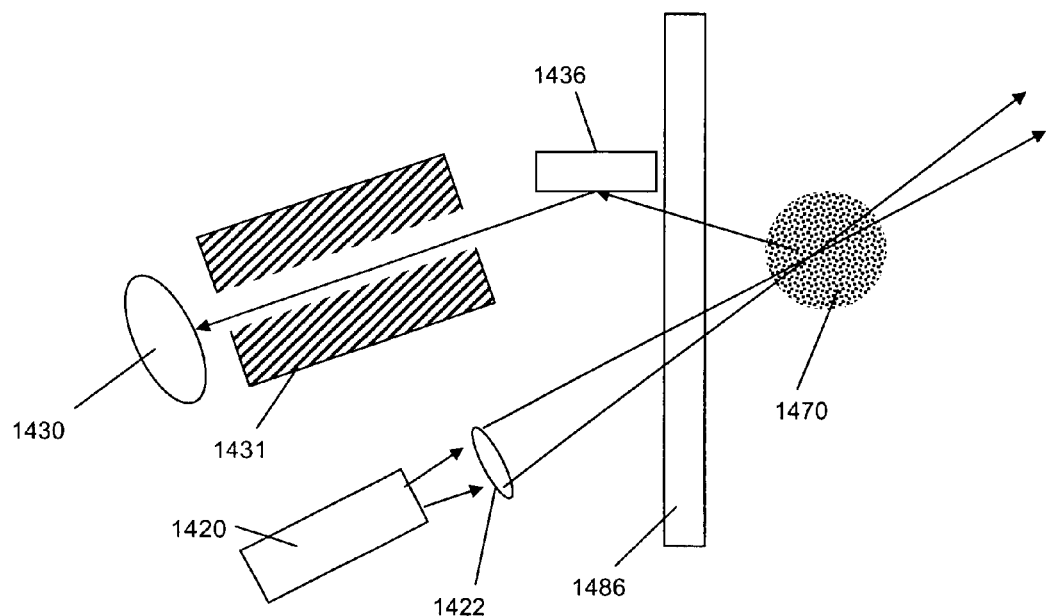
FIG. 14a depicts a diagram of an exemplary optical arrangement of the invention in which the detection optics comprise a mirror.
Figure 14B:
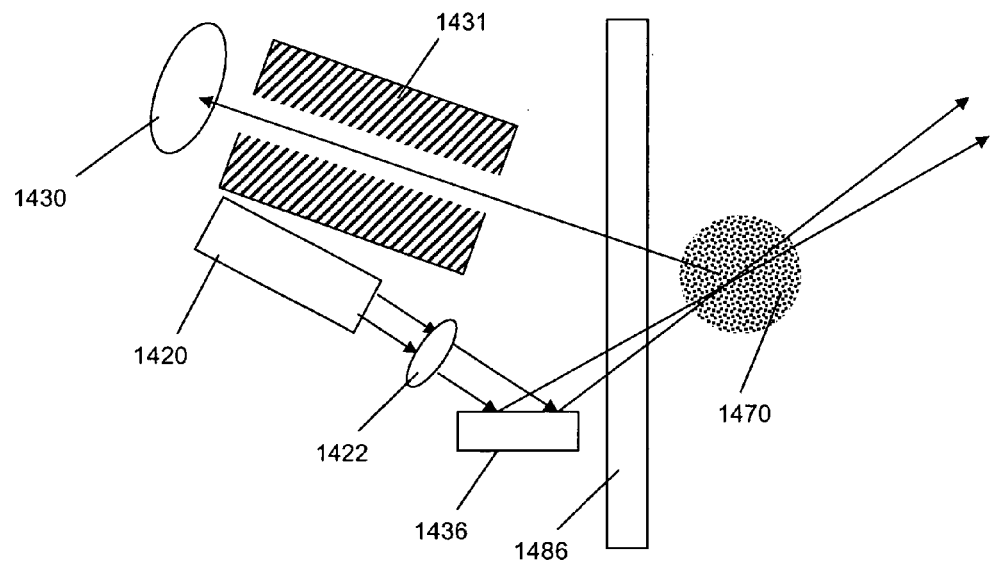
FIG. 14b depicts a diagram of an exemplary optical arrangement of the invention in which a mirror is used in the source optics.

Thus, in settings where the size of the sensor is of importance, use of mirrors can help in keeping down the overall size of the sensors of the invention. Further illustration of this can be seen in FIGS. 14*a* and 14*b* (which share numbering) which illustrate embodiments in which the sensor is made more compact while maintaining the spatial selectivity advantages described already. In FIG. 14*a*, mirror 1436 is used to deflect radiation emanating from medium of interest 1470 (originating from source 1420, focused through lens 1422, and passing through vessel wall 1486) into the detection optics. The mirror is oriented so that the angle between the optical axes of radiation source 1420 and detection aperture 1431 (and eventually detector 1430) is smaller than the angle at which the radiation beam and detection cone are overlapped within the medium of interest. In FIG. 14*b*, mirror 1436 is used to instead deflect the source radiation beam. In yet other embodiments, both the radiation source and detected radiation are deflected by mirrors.

Figure 9E:
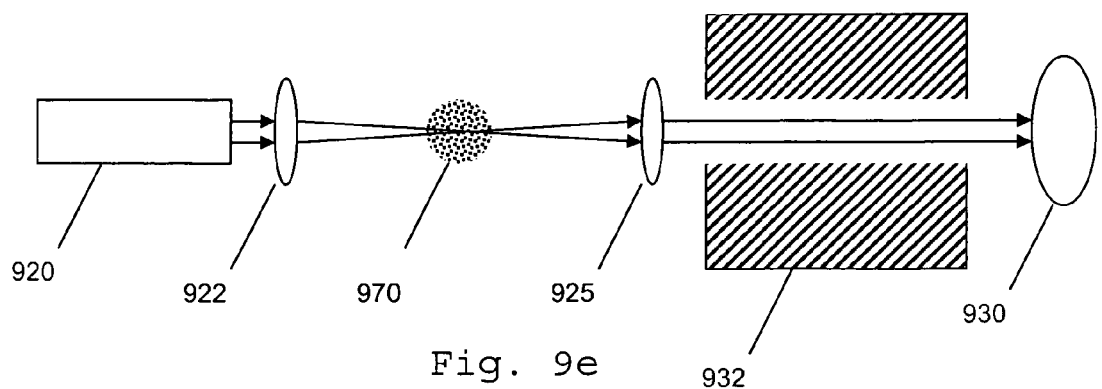
FIG. 9e depicts a diagram of an exemplary transmissive optical arrangement of the present invention employing a long aperture with a lens and an angled, focused laser.

Although the optical arrangements shown in FIGS. 9*a-d* depict the detection of scattered radiation, the methods and devices of the invention are readily adapted to the detection of transmitted radiation as well. As an example, the optical arrangement of FIG. 9*d* can be converted to the purpose of selective detection of transmitted radiation by placing the detection system in line with the radiation source, as depicted in FIG. 9*e*. In such embodiment, the distance between lens 922 and lens 925 can be adjusted to allow maximum transmission of the radiation beam through the aperture. This may be accomplished, for example, by setting the distance between the two lenses to be the sum of their focal lengths.

Figure 15:
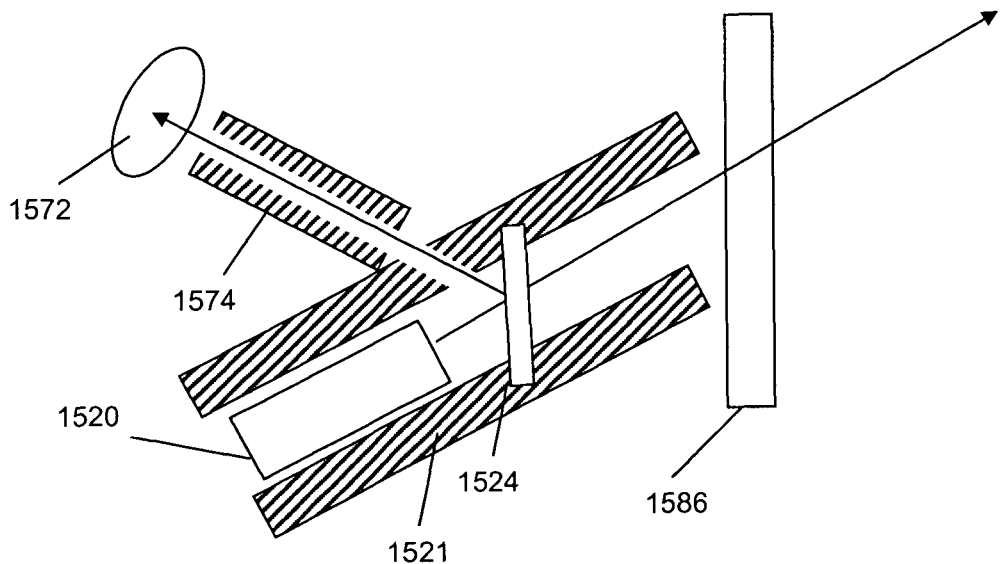
FIG. 15 depicts a diagram of an exemplary optical arrangement of the invention for monitoring the output of a source with low sensitivity to ambient radiation.

Some embodiments of the invention, include direct monitoring of the output of the radiation source. An exemplary optical arrangement for accomplishing this is depicted in FIG. 15. As can be seen, beam splitter 1524 is used to direct a portion of the radiation emitted from source 1520 towards radiation monitoring detector 1572. Detector 1572 is positioned so that substantially only radiation directly emitted by the source and reflected by the beam splitter will reach it. Ambient radiation is discriminated against by positioning the detector at the end of narrow aperture 1574 which can be made of material that is strongly absorbent to radiation. In some embodiments, the source is also confined within narrow aperture 1521. The angle between the optical axes of source aperture 1521 and monitoring aperture 1574 can be adjusted so that ambient light is substantially prevented from reaching monitoring detector 1572. As can also be seen in FIG. 15, the portion of the radiation beam not sent by the beam splitter to the monitoring detector, traverses vessel wall 1586 and can thus go into a volume area of interest.

In embodiments wherein multiple source-detector pairs are employed within a single sensor, various combinations of the above-described optical elements may be employed, as suited to the particular application. In one embodiment, the zone of overlap between the multiple source-detector pairs are arranged to be substantially coincident within the medium of interest. In another embodiment, wherein the sensor contains multiple detectors, the diameter or length of the detection aperture can be varied according to the angle between the optical axis of the radiation source and detection cone. Thus, as this angle is increased, the aperture diameter is increased or the aperture length is decreased. In other embodiments, a mirror can be used to deflect radiation for one or more source-detector pairs while one or more other source-detector pairs do not employ a mirror. Again, it will be appreciated that not all elements described herein will necessarily be present within all embodiments. Rather, various embodiments can optionally comprise any combination (including all) of the various elements herein.

Sensor Electronics

In various embodiments, the radiation level emitted by the radiation source is electronically controlled. The resulting signals from the different source-detector pairs are amplified and digitized for further digital processing. Thus, some embodiments of the invention can comprise amplifiers used to amplify various signals within the sensor. The electronics for accomplishing these tasks can be located within the sensor or can be located remotely from the sensor. In some embodiments the optical components are mounted directly to a printed circuit board.

A computer (e.g. a microcomputer or microprocessor) can also be provided in various embodiments for adjusting the source level and processing the measured signals according to the algorithms described herein. A memory storage device, either separate or integral to the computer can also be provided for storing instrument settings and calibration parameters, etc. In some embodiments the processed sensor signal is provided as a digital signal which can be read by a personal computer (PC) for display and manipulation. A protocol for allowing communication from the PC to sensor can also be provided to allow for the setting of operational parameters during manufacture and by end users.

Thus, as noted above, the various components of the present system are coupled to an appropriately programmed processor or computer that functions to instruct the operation of these instruments in accordance with preprogrammed or user input instructions, receive data and information from the components of the sensor, and interpret, manipulate and report this information to a user. As such, the computer is typically appropriately coupled to the instruments/components (e.g., including an analog to digital or digital to analog converter as needed).

The computer optionally includes appropriate software for receiving user instructions, either in the form of user input into set parameter fields, e.g., in a GUI, or in the form of preprogrammed instructions, e.g., preprogrammed for a variety of different specific operations. The software then converts these instructions to appropriate language for instructing the correct operation to carry out the desired operation (e.g., of arbitrating between signals from different source/detector pairs through use of the algorithms herein, etc.).

The computer can receive the data from the one or more sensors/detectors pairs included within the system, interpret the data, and either provide it in a user understood format, or use that data to initiate further instructions, in accordance with the programming, e.g., such as in continued monitoring of a sample until a particular biomass is reached, and the like.

Any controller or computer optionally includes a monitor which is often a cathode ray tube ("CRT") display, a flat panel display (e.g., active matrix liquid crystal display, liquid crystal display), or the like. Data produced from the current systems, e.g., particle concentration, is optionally displayed in electronic form on the monitor. Additionally, the data gathered from the system can be outputted in printed form. The data, whether in printed form or electronic form (e.g., as displayed on a monitor), can be in various or multiple formats, e.g., curves, histograms, numeric series, tables, graphs and the like.

Computer circuitry is often placed in a box which includes, e.g., numerous integrated circuit chips, such as a microprocessor, memory, interface circuits. The box also optionally includes a hard disk drive, a floppy disk drive, a high capacity removable drive such as a writeable CD-ROM, and other common peripheral elements. Inputting devices such as a keyboard or mouse optionally provide for input from a user and for user selection of sequences to be compared or otherwise manipulated in the relevant computer system.

In some embodiments, the devices and systems of the invention can comprise multiple computer (or microcomputer) components. Thus, for example, some embodiments can comprise a microcomputer present within the housing of the sensor (e.g., which can supply the proper algorithm instructions to process readings from the sensor, etc.) and/or within a base unit (e.g., which be used to control a user interface, can aid in communication between the sensor, a microcomputer within the sensor housing, a PC, etc.).

Exemplary Use and Component Variation

An exemplary embodiment of a sensor combining various aspects of the present invention is illustrated in FIGS. 1-4 (which share numbering). As can be seen in FIG. 1, optics nest 159 within inner housing 157 of sensor 158 holds optical components and provides apertures into and out of the sensor. A radiation source, laser 120, is placed within illumination aperture 121 in the optics nest (see also 1521 in FIG. 15). The illumination aperture limits the divergence of the laser beam in addition to serving as a mount for the optical components. The laser is focused by lens 122 (see also 922 in FIG. 9), passed through beam splitter 124 and face plate 126, and reaches a minimum diameter at point 128 outside of the sensor (e.g., inside a medium of interest). Cells or microorganisms within the medium scatter the laser light, some of which is reflected back towards the sensor. Reflected light is detected by one of three detectors, 130, 132, or 134 after passing through one of three apertures 131, 133, or 135. Aperture 135 for third detector 134 also includes mirror 136 that redirects the reflected light. A fourth detector (see, e.g., detector 1572 in FIG. 15) is positioned behind an aperture (see, e.g. aperture 1574 in FIG. 15) to detect laser light directly reflected by beam splitter 124 (e.g., splitter 1524 in FIG. 15). The exemplary embodiment in FIGS. 1-4 also includes light pipe 152, cable 154, cable gasket 156, and vessel 160.

The laser and detector components in the illustrated embodiment are positioned so that the laser beam overlaps maximally with the detection beams at approximately the same point, point 128, for all three detectors. The detection beam is defined as the cone within which reflected light may travel to reach the detector. The term "zone of overlap" is used to indicate the region within the medium in which the laser beam overlaps spatially with at least one of the detection beams. The center of each detection beam is depicted by a dashed line in FIG. 1. The point at which the laser beam overlaps maximally with the detection beams also approximately coincides spatially with the point at which the laser beam reaches a minimum diameter. See also FIG. 9b.

Figure 2:
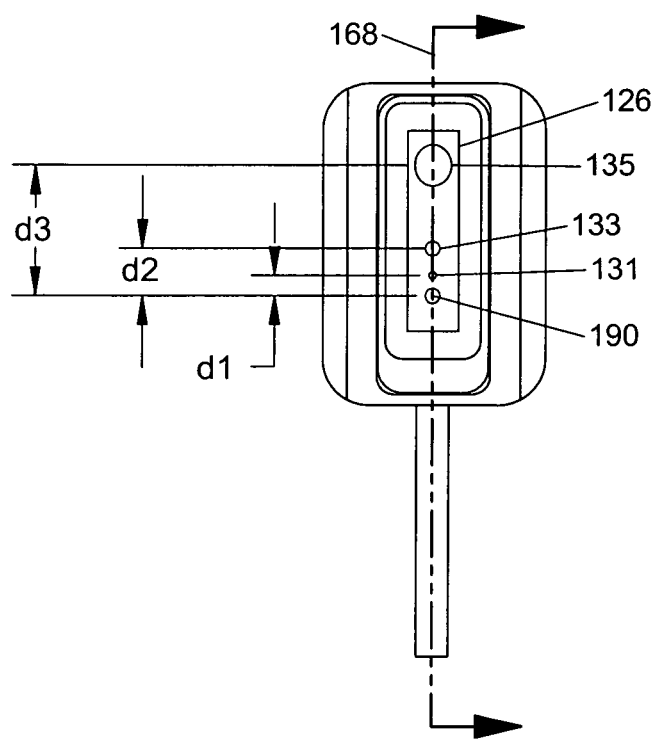
FIG. 2 depicts a front face view of an exemplary sensor of the present invention designed for mounting to the exterior of a vessel.
Figure 3:
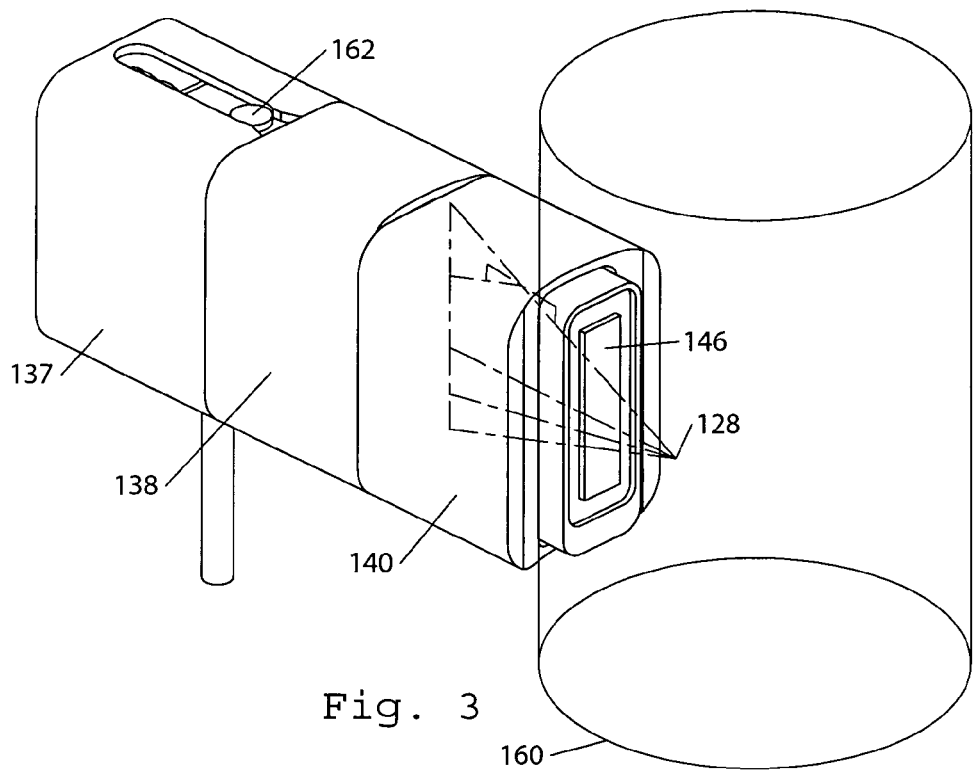
FIG. 3 depicts an isometric view of an exemplary sensor of the present invention in relation to a vessel.
Figure 4:
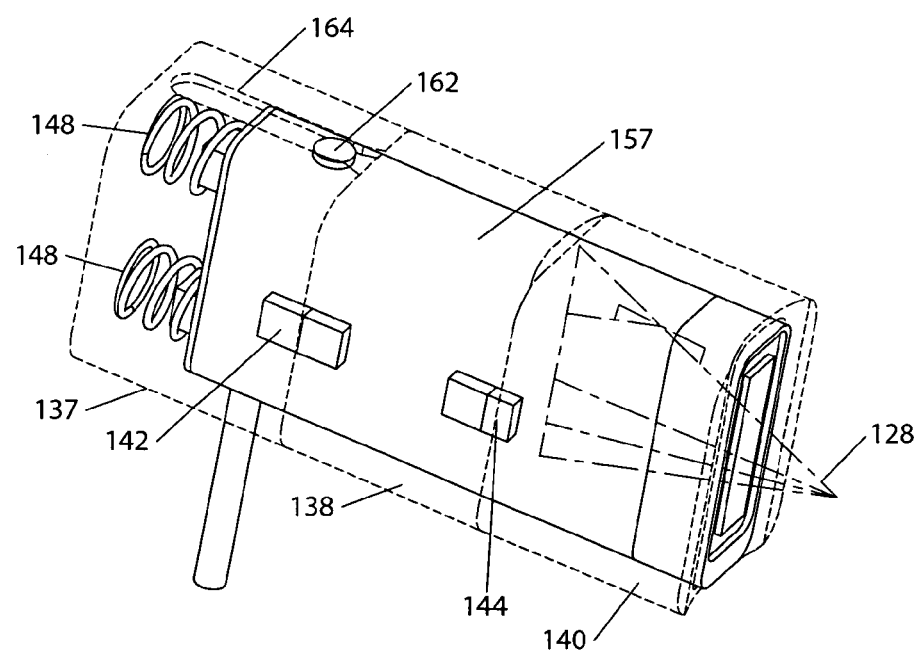
FIG. 4 depicts an isometric view of a an exemplary sensor of the present invention, with the exterior shell made semi-transparent for illustrative purposes.

FIG. 2 illustrates that the laser and detector components are arranged so that line 168, bisecting the front of sensor face plate 126, intersects with the laser beam and all three detection beams. Along this line, the distances between the center of the laser beam (center 190) and each of the detection beams ($d_1$, $d_2$, and $d_3$ in FIG. 2), are approximately 3, 6, and 18 mm, respectively for the first, second, and third detectors in this embodiment. The length of the three detection apertures, apertures 131, 133, and 135, are all approximately 20 mm. The width of the three detection apertures are 1, 2, and 5 mm, respectively at the point at which they intersect with the face plate. The first detection aperture, aperture 131, can have a wider diameter near the detector, to facilitate fabrication.

A suitable laser for use in various embodiments of the invention is a near infrared diode laser, such as from US Lasers (Baldwin Park, Calif.). For example, part number D850-5 from US Lasers can be utilized in various embodiments of the invention. This laser is compact and emits a narrow beam of light at 850 nm. A suitable lens for focusing the laser can comprise, e.g., lens part number NT32-022 from Edmund Optics (Barrington, N.J.). This lens has a 3 mm diameter and a 4.5 mm focal length. Suitable detectors for first detector 130 and second detector 132 can be such as those from Advanced Photonix (Camarillo, Calif.), e.g., part number PCB-C134F. A suitable detector for third detector 134 can be a detector such as part number PDB-C142F from Advanced Photonix. A suitable detector of the fourth detector (e.g., such as 1572 in FIG. 15) can be a surface-mount detector such as part number PDB-C160SM from Advanced Photonix. Beam splitter 124 can be constructed from any optical material that is partially transmissive and partially reflective at the wavelength light emitted by the laser. In some embodiments, the beam splitter is constructed from uncoated glass or plastic, having the property that only a small fraction of the laser light is diverted towards the fourth detector. The material used to construct sensor nest 159 is ideally highly absorbent of light emitted by the laser. An example of a suitable material is black ABS. Of course, it will be appreciated that specific recitation of examples of components used within the illustrated embodiment, should not necessarily be taken as limiting and that other component lenses, radiation sources, etc., can also be used in different embodiments of the invention.

The front face of the sensor in the illustrative embodiment is covered with face plate 126 that protects the sensor from the environment in which it is operated. The face plate can be constructed from a material that is transmissive to light emitted by the laser. In addition, the face plate can be absorptive to light at wavelengths other than the laser emission wavelength. An example of a suitable material for the face plate is Edmund Optic part number NT 43-954, which is transmissive to near infrared light but absorptive to visible light. Surrounding the face plate is gasket groove 146 (FIG. 3) used to contain a gasket. The gasket groove helps to prevent the gasket from moving and possibly obstructing the face plate. When pressed against a vessel wall, the gasket creates a seal that prevents materials from occluding or affecting the optical measurement.

As illustrated in FIGS. 1-4, the sensor optics nest is contained within inner housing 157 that is connected to rear outer housing or shell 137. The inner housing and rear outer housing are connected by springs 148, spring shafts 150, and locking pin 162 in inner housing 157 and mating channel 164 in rear outer shell 137. The inner housing slides within the outer shell under constraint of the springs and channel. Channel 164 contains a section with reduced width that prevents the accidental separation of inner housing 157 from the rear outer housing. However, intentional separation of the inner and rear outer housing may be achieved by applying sufficient manual force to temporarily widen the channel past the locking pin.

Mid-section 138 is attached to the rear section of the outer shell. The mid-section is shaped to surround the inner housing, and has a flat face on the end facing the rear section and a curved face of the end facing the front of the sensor. Coupling between the rear and mid-section of the outer shell can be achieved by many different mechanisms, but in some embodiments, magnetic coupler 142 and/or coupler 144 is/are used. By embedding magnetic couplers in both the rear and mid-section of the outer shell and by proper orientation of the magnets, the user may be prevented from incorrectly orienting the mid-section of the outer shell. In some applications, front section 140 can also be attached to the mid-section of the outer shell. The front section of the outer shell is similar in construction to the mid-section, having a flat end facing the rear of the sensor and a curved end facing the front of the sensor. However, the length of the front section of the outer shell may differ from the mid-section. Coupling of the front section to the mid-section of the outer shell may be achieved in analogous manner to the coupling of the mid-section to the rear section of the outer shell.

In some embodiments, the sensor can be attached to the exterior of a vessel such as a bioreactor or fermentor that contains medium and cells or microorganisms. A latch and strap can be attached to the back side of the sensor. The strap can be used to encircle the vessel by means of a buckle. After the strap is tightened into the buckle, final compression of the sensor against the vessel is achieved with the latch. Those of skill in the art will be familiar with this method of strapping a sensor to a vessel (e.g., from U.S. Pat. No. 7,100,462) as well as other methods of connecting sensors and similar devices to various vessels and which can optionally be used with various embodiments of the current invention.

In some embodiments, a calibration cup can be attached to the front of the sensor in place of a vessel. The calibration cup contains a reflective material which is relatively unchanging with time. See below for more description of calibration. In some embodiments two calibration cups are provided for use with the sensor. The two calibration cups provide low and high reflectance signals. Suitable, but not necessarily limiting, materials for providing the low and high reflectance signals, respectively, are black ABS and Kynar. Through the use of shorter front sections or the complete removal of the front section of the outer shell, the sensor may be quickly adapted to fit within narrow, recessed viewing ports. Different length front sections may be employed depending on the depth of the port.

For the purpose of sensor calibration during instrument manufacture a series of several calibration standards with varying reflectance can be provided. A suitable material for providing such a variable reflectance signal is acrylic with variable amounts of a scattering substance, such as titanium oxide, mixed in prior to polymerization. Alternatively, a liquid suspension of particles at a range of concentrations may be used for sensor calibration. An example of such a liquid suspension is Baker's yeast dissolved in water containing 0.9% (w/v) sodium chloride. Many alternative materials can also used for this purpose. For example, polymer spheres, such as polystryrene micro-spheres, which can be used over an extended period of time. Another advantage of the use of polystyrene spheres is that they may be prepared in a highly reproducible fashion, with a narrow distribution of particle diameters.

Electronics for controlling and driving the radiation source and for amplification of the detected signal, etc., can be provided by an electronic board, such as board 166, contained within the inner housing of the sensor. Circuits and algorithms for electronic control, etc., that can be included within an electronic board, are described in U.S. Pat. No. 6,573,991. Again, those of skill in the art will be familiar with other electronic boards, etc., that can be used with various embodiments of the invention. In many embodiments, the detected signals are digitized, processed, and combined, and sent to a base unit.

In various embodiments, the base unit displays (e.g., via a monitor) the measured result on a screen, and converts the result into various analog and digital forms for presentation to a user. The output results can be provided in digital form by means of RS-232, USB, and/or Ethernet connections and in analog form by means of a 4-20 mA current output or 0-10 V voltage output. Additional functions of the monitor can include providing a means for accepting user input. Switches in the monitor can be provided that allow the user to select the analog output range as well as the time constant with which output results are averaged. Additional switches or buttons can be used to allow the user to set and turn on or off the usage of a baseline value which is subtracted from all subsequent output values. Another switch can be used to turn on or off the application of a user-defined calibration. In some embodiments of the invention, some or all of the switches described above are replaced with a keypad interface. The keypad interface can be used in conjunction with an alphanumerical or graphical display to select and set various features and variable values. In one embodiment, the sensor optical components (i.e. lasers and detectors) are mounted directly to the sensor board. In another embodiment a flex circuit is used to connect the optical components to the board.

In some embodiments herein, the devices of the invention display a characteristic related to concentration of a type of particle within a medium rather than displaying the concentration itself. Thus, for example some embodiments of the devices herein can display, e.g., OD, turbidity. Thus, when the devices and methods are described throughout, it will be appreciated that they can comprise embodiments wherein the device/method displays or reports a concentration related characteristic such as OD or turbidity rather than the concentration of the particle type (e.g., in numbers of particles per unit volume).

Algorithms and Operation of the Invention

Theories of operation of the invention are provided as an to aid to the understanding of the invention, however, particular theories of operation should not necessarily be taken as limiting upon the methods and devices of the invention.

Algorithms for Combining the Sensor Signals—Arbitrating

In the various embodiments herein, the invention comprises methods having algorithms for combining the individual emitter-detector signals (i.e., the signals from multiple source/detector pairs) into a single result related to particle concentration. By experimental measurement of radiation transmitted and/or reflected through media containing varying concentrations of particles, the inventors have found that the broad relationship between detected radiation and particle concentration is a non-linear function. However, by sufficiently narrowing the range of measurement of particle concentration it is possible to define a region within which the relationship between detected radiation intensity and particle concentration is linear and thus more accurate. Further by varying the geometric relationship between the radiation source and detector (i.e., by having multiple source/detector pairs at different orientations/placements), the methods of the invention allow the range of particle concentrations over which a linear response is observed to shift. The present invention includes wherein, by a careful selection of source-detector geometries, multiple signals can be combined into a single sensor response having a linear dependence on particle concentration, over a much wider concentration range than that of any single source-detector pair.

In general, the combining of the individual source-detector pairs includes the steps of: (1) identifying the source-detector pair or pairs having the most linear response at a particular particle concentration, and (2) mathematical manipulation of these selected individual source-detector signals so that the linear function matches that produced at other particle concentrations as measured using other source-detector pairs.

Identification of the source-detector pair having the most linear response at a particular particle concentration can be accomplished in several ways. In some embodiments the invention arbitrates between the various source/detector pair signals. Thus, the signal level from individual source-detector pairs are compared to pre-determined threshold values. Such threshold values can be determined during calibration of the sensor during manufacturing. The threshold value can be found by measuring reflectance/transmission of a number of known different particle concentrations (e.g., at least 5, at least 10, at least 15, at least 20, at least 25, at least 50, or at least 100 or more concentrations) with each source/detector pair of the sensor. The threshold values for each source/detector pair are the reflectance/transmission values beyond which the values no longer show linearity with concentration. The threshold level for a given source-detector pair may consist of an upper or lower threshold or both. Threshold levels can be predetermined for (and are typically specific for) each source/detector pair and, in some embodiments, can be predetermined not only for each source/detector pair, but also for particular types of particles (e.g., yeast cells, etc.). If the signal from a particular source-detector pair falls within the bounds of the threshold values, then that signal is determined to be within a linear range of response and is used in or as the final result. If the signal falls outside the bounds of the threshold values, the signal is determined to be outside of its linear range of response and is not used in the final result.

Figure 11A:
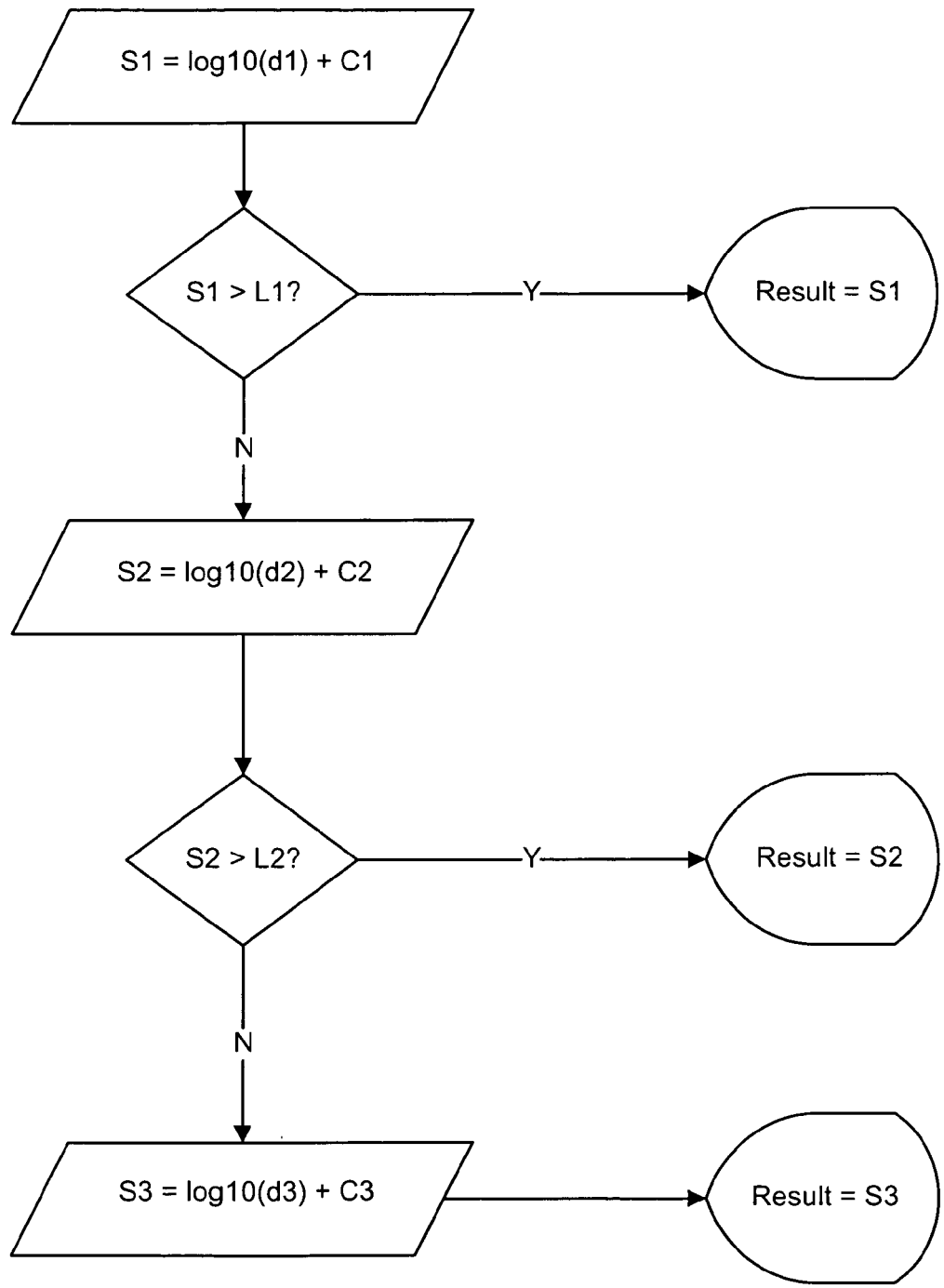
FIG. 11a presents a flow diagram summarizing an algorithm for arbitrating between three source-detector signals and producing a single output.

In some embodiments, it can be advantageous to compare source-detector signals to threshold values in a specific sequence. See also FIG. 11a. This is particularly useful when some source-detector pairs provide signals levels that may be indicative of more than one concentration. For example, referring to FIG. 5a (described in more detail below), when a reflectance intensity measured from a source-detector pair spaced 28 mm apart (depicted by circles in FIG. 5a) has a value of 0.01, the corresponding concentration could be either 2 g/L or 50 g/L. The inventors have generally found that this type of non-monotonic response to concentration is most pronounced for widely separated source-detector pairs. In order to avoid ambiguity in the source-detector selection, the threshold comparison can first applied to the most closely spaced source-detector pair. If the closest spaced source-detector pair is greater than a first threshold value, then it is determined to have the most linear response to particle concentration, it is carried forward to the final result, and no further threshold comparisons need to be made. If the closest spaced source-detector pair is below the first threshold value, then the next closest spaced source-detector pair is selected for threshold comparison. If the second closest spaced source-detector pair is greater than a second threshold value, then it is determined to have the most linear response to particle concentration, and so forth. In this manner, widely spaced source-detector pairs are often only used for threshold comparison when their signal levels are known to fall within a region of monotonic response to concentration.

Once the source-detector pair or pairs having the most linear response to concentration have been identified at the current concentration level, the second algorithmic step is to mathematically manipulate the signal(s). During calibration of the sensor, the various lines plotting reflectance/transmission versus concentration for each source/detector pair are mathematically manipulated to "line up" the slopes of their respective areas of linearity. The offsets and multiplication factors necessary to be applied to the data from each source/detector pair in order to do so during calibration, are then applied to the reflectance/transmission values obtained during actual usage of the sensor. Mathematical manipulation of the reflectance/transmission values can include multiplication of the values or addition of an offset to the value (typically done as addition of a value to the log of the reflectance/transmission signal value). The offset and/or multiplication values are typically pre-set, along with the necessary algorithms, into the computer, microcomputer, or memory component of the sensors of the invention.

Figure 5A:
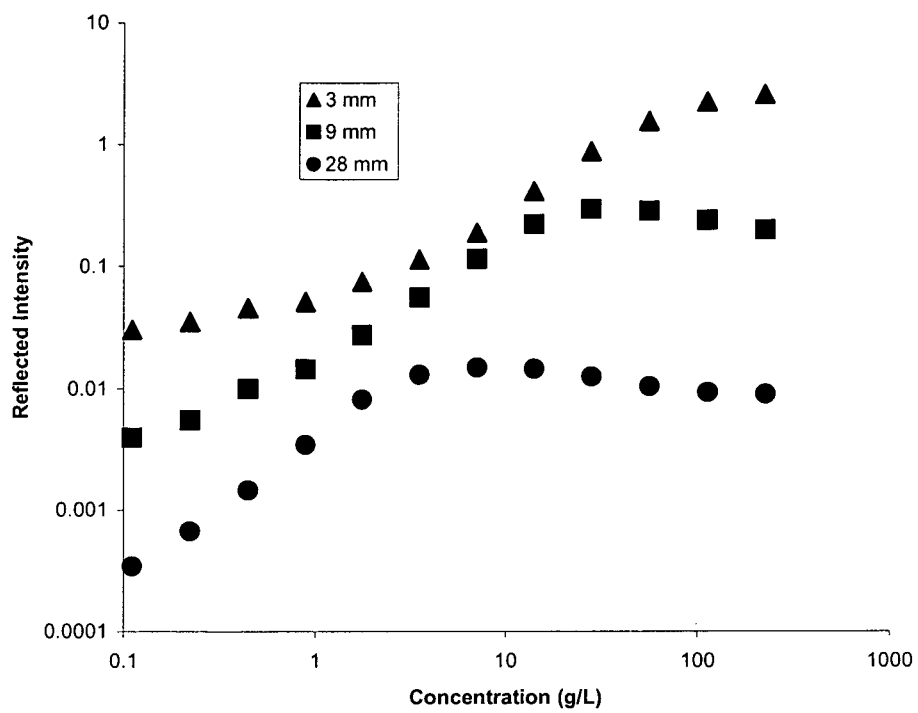
FIG. 5a presents a graph of the response of three source-detector pairs at three different separation distances measuring reflectance from yeast in a bioreactor.
Figure 5B:
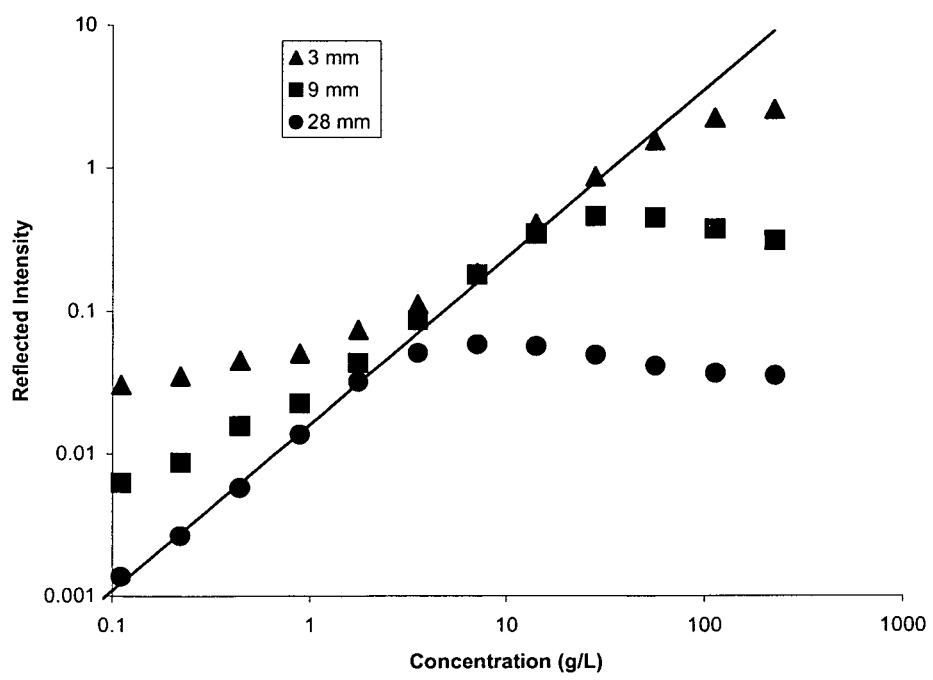
FIG. 5b presents a graph containing the same data as in 5a except the responses of the source-detector pairs separated by 9 and 28 mm have been offset according to an algorithm of an embodiment of the present invention.

An example (further described below) of mathematical manipulation of signal values is illustrated in FIGS. 5a and 5b, in which the raw reflectance signals measured from three source-detector pairs (FIG. 5a) are mathematically manipulated so that they line up to form a continuous linear response across a wide range of concentrations (FIG. 5b). Manipulation modifiers (offsets, etc.) determined from measurements as in FIG. 5 can then be applied to values measured from various media, etc. when analyzed with such source/detector pairs. In one embodiment of the invention, this mathematical manipulation consists of multiplying each of the source-detector signals by a pre-determined factor (F). This factor can be (and often is) different for each source-detector pair and is typically determined during manufacture as a calibration step (described further below). In another embodiment, both an offset and multiplication factor are applied to each source-detector pair. In yet another embodiment, a multiplication factor (F) and two offset terms (O1, O2) are applied to the logarithm of each source-detector pair, according to:

$$S = F \log(S + O1) + O2 \quad \text{(Equation 2)}$$

In the equation, F is a multiplication in log space, while $O_1$ is a multiplication in linear space and $O_2$ is an offset. In alternative embodiments of the invention, the order of the two steps in the algorithm is reversed: the source-detector signals are mathematically manipulated before arbitrating between them. Manipulation of the source-detector signals prior to threshold comparison may have the benefit of allowing the same thresholds to be applied across multiple sensors, rather than having to set the thresholds on a sensor-by-sensor basis.

In another embodiment of the algorithm, the arbitration decision can result in the selection of more than one source-detector pair in some concentration regions. This can arise, e.g., when the particle concentration produces a reflectance/transmission value that falls within the range of linearity for more than one source/detector pair. This may also be desirable, for example, so that a smooth transition is achieved when switching between concentration ranges in which different source-detector pairs are selected. In one embodiment, a linear function is used to combine source-detector pairs in transitional concentration regions. The implementation of such a linear function is detailed below as an example. See FIG. 11b The appropriate threshold values and/or widths of transition regions described in the above algorithms will vary depending on the sensor geometry (e.g., the particular source/detector pairs). Even for sensors manufactured to be as similar as possible, some variation in the constants and levels may be beneficial to sensor performance. Therefore, it can be desirable to determine optimum levels of these variables subsequent to the assembly of each sensor.

Algorithms for Combining the Sensor Signals—Combining

According to above algorithm of the invention (see also FIG. 11a), the signals from the individual emitter-detector pairs are manipulated and selected-between to create a combined response. However, rather than simply arbitrating between the signals, in other algorithms of the methods herein the individual emitter-detector signals may be mathematically combined. Such combination uses weighting factors to emphasize the contribution, from source-detector pairs that provide the most linear response to changes in particle concentration, at the particle concentration currently under measurement. In one such alternate algorithm, the signal from the detector closest to the emitter ($D_1$) is used to create a weighting factor, W:

$$W = C_1[\log_{10}(D_1) - C_2] \quad \text{(Equation 3)}$$

where $C_1$ and $C_2$ are coefficients whose optimal values may be determined and stored in device memory during sensor manufacturing. This weighting factor is then used to mathematically combine the three emitter-detector signals ($D_1$, $D_2$, $D_3$) according to:

$$C_3 * W * \log_{10}(D_1) + C_4 * (1-W) * [\log_{10}(D_2) + C_5 * \log_{10}(D_3) + C_6] \quad \text{(Equation 4)}$$

where $C_3$ through $C_6$ are coefficients whose optimal values may be determined and stored in device memory during sensor manufacturing. This method of combining the emitter-detector pairs has the advantage of extending the range of linearity in the high particle concentration range by two means: (1) The function has a quadratic dependence on the logarithm of the signal from the closest spaced source-detector pair (D1), (2) At the highest particle concentrations, the function takes advantage of the fact that the D2 and D3 signals roll over with increasing particle concentration, by adding an increasing negative weighting to these signals with increasing particle concentration. In practice, coefficients C1-C6 can be determined during manufacture by measuring the source-detector signals across a range of particle concentrations. The C1-C6 values are varied in a search that minimizes the difference between the result of equation 4 and the particle concentration across a range of concentration values. Minimization search methods are well known in the art. Appropriate methods include, for example, the Levenberg-Marquardt algorithm and the simplex algorithm. Once the values providing optimal linearity have been determined, C1-C6 may then be stored in memory for later retrieval and application when measuring a medium containing an unknown level of particle concentration.

Calculation of the Rate of Change in Particle Concentration

In some embodiments herein, the methods of the invention can be used to determine the rate of change in concentration of a particle type in a medium. Due to the high linearity of the sensor response with respect to changes in particle concentration, the rate of change of the concentration as a function of time can be accurately calculated by the present invention in a short period of time. Although various methods of computing the rate of change may be applied, in one embodiment, linear regression is used to determine the slope of a function of the sensor response vs. time. This aspect of the invention is especially useful in instances involving measuring a growth rate of a microbial or cell culture. In such instances the slope of the logarithm of the sensor response versus time will be a particularly useful quantity. When the biomass (B) in the culture is growing exponentially, the slope determined will be the growth rate constant (k), as shown in equation 5, below:

$$B = B_0 e^{kt} \quad \text{(Equation 5)}$$

$$\ln(B) = kt + \ln(B_0) \quad \text{(Equation 6)}$$

Alternatively, the growth rate can be converted to a doubling time ($t_2$) as shown in equation 7, below:

$$t_2 = \frac{\ln 2}{k} \quad \text{(Equation 7)}$$

Note that the determination of the growth rate (or doubling time), does not require an absolute measurement of biomass, but only that the sensor response be linearly related to biomass. Thus, even without calibration of the sensor to specific biomass units, the absolute growth rate can be determined. In one embodiment of the invention, the growth rate is computed in real time by a recursive estimation of the slope, according to equation 6, and provided, on its own or in conjunction with an estimation of biomass, as an output to the user.

Reducing Sensitivity to Environmental Variables

The present invention also provides methods for compensating for environmental factors that affect the behavior of the source or detection components in the sensor. Such environmental factors may include variations in temperature, ambient radiation, humidity, dust, and other contaminating gases, liquids, and solids. In one embodiment, a portion of the radiation emitted by the source is used to directly monitor the output of the source. An example embodiment, in which a beam splitter 1524 is used to reflect a portion of the radiation from source 1520 onto a source monitoring detector 1572, is illustrated in FIG. 15. In one embodiment, the signal measured by the source monitoring detector is used as a feedback to control the output of the source. In another embodiment, the signal measured by the source monitoring detector is used to normalize signals measured by other detectors, positioned to measure radiation that has interacted with the medium of interest.

Several methods and devices of the invention help to reduce the effect of ambient radiation on the detector response. In a first method, a sensor window through which the radiation travels to and from the sources/detectors, is provided that is substantially transparent in the wavelength range emitted by the source but substantially non-transmissive to radiation in other wavelength ranges. In a second method, one or more of the detectors are place behind a filter that is substantially transparent in the wavelength range emitted by the source but substantially non-transmissive to radiation in other ranges. In a third method, the light source is modulated and phase sensitive amplification is used to measure the detector signals. Appropriate methods of light source modulation include amplitude, frequency, or polarization modulation. Such methods are further described in U.S. Pat. No. 6,573,991 which is incorporated here by reference. In a fourth method, apertures are used to discriminate against ambient radiation in favor of radiation emitted by the source.

In various embodiments, the effect of contaminants on the sensor signal can be mitigated in several ways. In a first method, the sensor is sealed to impede the ingress of contaminants into the sensor enclosure. In a second method, a compressible gasket is used to surround the sensor window to prevent contaminants reaching the space between the sensor and vessel during measurement. In a third method, electronic components are coated with a material that impedes contaminants from coming into contact with the components. Conformal coatings of electronic boards are well known in the art and may be accomplished using materials including, e.g., acrylic, epoxy, polyurethane, and silicone.

Calibration

Sensor Calibration, Protection, and Performance Verification

When not in use, the sensor can be protected by a cup that surrounds the front face of the sensor. This cup can also be used to check the performance of the sensor. In one embodiment, the cup contains the material Kynar™. During manufacture, the reflectance of the cup can be determined by applying radiation from the source(s) within the sensor and measuring the resulting signals from all source-detector pairs. These signal levels are recorded in the memory of the sensor or attached monitor, etc. In later use, the proper functioning of the sensor can then be determined by comparing the signal levels measured on the cup to those values stored in memory. If the measured signal levels fall outside of a predetermined range, warnings or error messages can optionally be reported to the user.

In some circumstances it may be desirable to recalibrate the sensor. For this purpose, two calibration cups providing low and high signal levels can be used. By combining the results from the two calibration cups both the offset and gain of the detector amplifiers can be separately determined. The measured offset and gain are stored to memory, and used to compensate subsequent measurements. In this manner, drift of the electronic components over time can be compensated by the user. In such embodiments, a software-guided routine can be provided for users to follow.

In one embodiment, a sensor measurement of the calibration cups is performed during manufacture, the result of which is stored for later use, for example, by electronic means within the sensor. During subsequent usage, the calibration cup measurement may be repeated by the user. See above. A number of repeated measurements of the calibration cups can be used to improve the accuracy of the measurement and to verify that the calibration cups are stably attached to the sensor. In such methods, the mean and standard deviation of the repeated measurements are computed. If the standard deviation exceeds a threshold value, the user is instructed that the measurement was unstable. The mean of the measurements is used for comparison to the values stored during manufacture. Stored thresholds are then used to provide the user with a pass/fail determination. The option of recalibrating the sensor is provided in many embodiments. In some circumstances it is beneficial to force the user to check the performance of the sensor using the calibration cups prior to its usage for other measurements, therefore an electronic timer within the sensor can be used to determine the frequency of such tests.

During instrument manufacture, methods of compensating for sensor-to-sensor differences can also be provided by calibration materials. In one embodiment, a series of approximately 10 calibration standards are used. The standards are constructed to have a range of reflectance properties, similar to the materials which will be monitored in later usage (e.g. cells in a liquid culture). The sensor signals on each of the 10 calibration standard is measured. The signals are then used to determine sensor calibration coefficients. For example, the calibration coefficients $C1$, $C2$, $C3$, $t1$, $t2$, $w1$, and $w2$ as shown in FIGS. 11$a$ and 11$b$, can be among those calibration coefficients that are varied based on the measurements of the calibration standards. In one embodiment, metrics for selection of the calibration coefficients include the linear correlation coefficient of combined sensor response versus particle concentration. After applying the calibration coefficients, if the sensor response versus particle concentration still contains significant non-linearity, the linearity may be further improved by fitting a function to the data or by creating a lookup table for interpolation between points. For example, after applying one of the algorithms of the present invention for combining the individual source-detector responses into a single response, the combined response may be compared to a list of combined responses in lookup table. The lookup table may consist of pairwise values of combined responses and values related linearly to particle concentrations. After finding combined response values bracketing the current combined response, interpolation may be used to convert to combined response to a value more linearly related to particle concentration.

Particle-Specific Sensor Calibration

In addition to the calibration steps described above to achieve wide dynamic range and reduce sensor-to-sensor variation, the further step of calibrating the sensor response towards the specific particle to be detected can also be useful in many applications. For example, in embodiments wherein biomass is being determined, the sensor can provide a readout in units that are most appropriate for the particular microorganism or cell type that is being measured. In one embodiment, polynomial regression coefficients relating the raw sensor response to the particle-specific response are written into the memory of the instrument and used to convert the sensor response into the desired units. Thus, for example, a handheld embodiment of the invention that is used to measure OD of bacterial culture (i.e., displays OD measurement of bacterial culture) could thereby be used to measure the OD of a yeast culture as well because the calibration allows conversion between the two different culture types. Several sets of coefficients can be stored within the memory of each sensor, providing the user with the option of selecting the mode of sensor output most appropriate for the present application. During manufacture, these application-specific calibrations can be written into sensor memory. Alternatively, users are able to add their own specific calibrations into the sensor memory.

In one embodiment in which a rapid "spot check" measurement of particle concentration is being made, a particle-specific selector is provided on the body of a sensor itself. For the specific application of measuring the optical density in small vessels such as shake flasks, the relationship between optical density and sensor response may differ according to cell size or other factors. In this application the user can be provided with the ability to select the cell type (e.g. "*E. coli*" or "*S. cerevisiae*") in order to improve the accuracy of the optical density measurement.

Hand-Held Sensors and Immersible Probes

Figure 10:
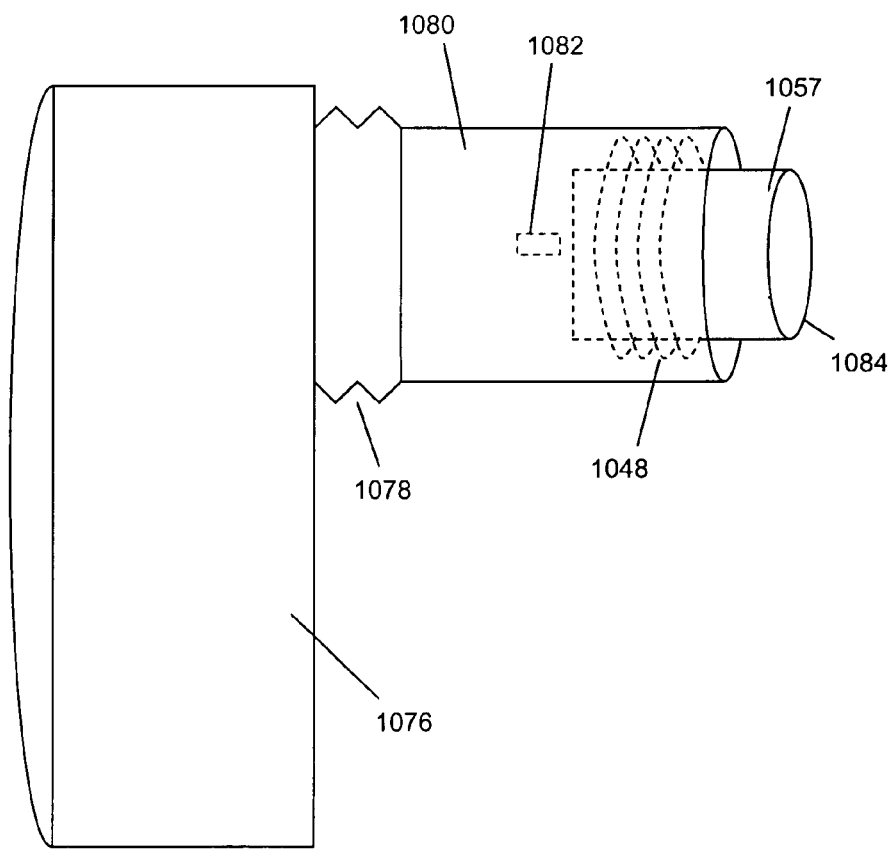
FIG. 10 depicts a diagram of an exemplary sensor of the present invention designed for performing spot-check measurement through vessel walls.

In some embodiments of the present invention, the invention allows users to perform rapid successive measurements on multiple containers. A sensor configuration adapted for this application is illustrated in FIG. 10. As can be seen, inner sensor housing 1057 can form an interface with the glass wall of the flask. The inner housing acts as a piston within outer sensor housing 1080. Spring connection 1048 between the inner and outer sensor housings is used to determine the force required to activate trigger 1082 which starts a reflectance measurement. The outer sensor housing is attached to handle 1076 via joint 1078 that allows the sensor face to pivot in all directions relative to the handle. As the user presses the sensor onto the shake flask, the sensor will automatically pivot to form a flat interface with the flask (at point of contact with vessel 1084). Sensor readings are output to a display on the handle of the device. Readings are not posted unless the trigger has been continuously depressed for a minimum time period (e.g. 3 seconds) during which the reflectance data is acquired.

Figure 18:
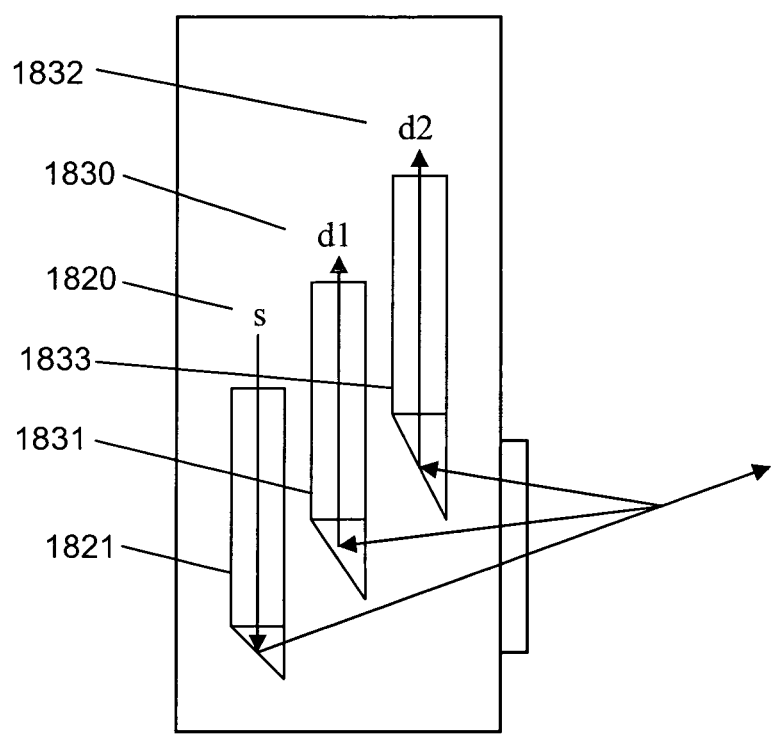
FIG. 18 depicts a diagram of an exemplary reflective optical arrangement suited for use as an immersible probe.

Although many of the embodiments described herein make reference to measuring through a vessel wall or window, many aspects of the invention are also applicable to immersible probes. One embodiment, designed to fit through a narrow port, such as is typically found in a bioreactor, is depicted in FIG. 18. In this embodiment the radiation source (source 1820) is confined to narrow aperture 1821 within the probe and then reflected at an angle towards the medium of interest. Similarly, after interacting with the medium, radiation is reflected at an angle into narrow apertures (apertures 1831 and 1833) toward radiation detectors (detectors 1830 and 1832). In some embodiments, the narrow apertures are optical fibers. The reflectors at the ends of the fibers can be integral or separate from the fibers. In some embodiments the reflectors are constructed by cleaving the fibers at an angle and coating the end of the fiber with a reflective material, such as a thin layer of silver. By varying the angle of the reflectors relative to the apertures, it is possible to keep the apertures parallel while varying the relative beam angle and size of the source and/or the angle of the detection cones. Although a single source and two detectors arranged in reflectance mode are depicted in FIG. 18, as with the non-immersible embodiments, the invention is readily extended with additional detectors, and is also applicable to transmissive optical arrangements, arrangements with a single detector and multiple sources, as well as optical arrangements employing multiple sources and multiple detectors.

In yet other embodiments, the sources and/or detectors are located externally to the body of the sensor or probe. Fiber optics can be used to transport the radiation between the probe body and the active optical elements (source and detectors). This design can be of particular utility as a single use probe. A connector (e.g. a fiber optic coupler) can be provided to allow the quick exchange of the disposable probe. The probe can also optionally be built into, or provided as, an integral part of a disposable bioreactor bag.

EXAMPLES

The following are examples of methods and use of devices of the invention (e.g., for determination of particle concentration). It will be appreciated that such descriptions and examples are not necessarily limiting upon the current systems, methods, etc. and their use unless specifically stated to be so.

Example of Algorithm Applied to Reflectance Measurement of Biomass

In this example, some of the algorithms of the present invention are applied to experimentally measured reflectance data. Measurements were made through the glass wall of a vessel containing a wide range of concentrations of *Saccharomyces cerevisiae* suspended in isotonic (0.9% w/v) saline. Such measurements can thus be used to determine offsets/multiplication factors to apply to measurement of unknown samples. See above. In the sensor used for this example, the source was a Vertical Cavity Surface Emitting Laser (VCSEL) emitting approximately 3 mW of power at 850 nm with a 3 degree divergence (Part No. SMV2637-001, Honeywell, Morristown, N.J.). The detector was a plastic lensed silicon photodiode (part no. PDB-C134F, Advanced Photonix, Camarillo, Calif.). The laser was angled at approximately 14 degrees from normal. The three source-detector signals were measured by moving the same detector in precise increments relative to the laser. The detector was angled at approximately 17 degrees from normal. The laser and detector were in direct contact with the vessel under measurement (no lenses or apertures were employed in this experiment). The reflectance signals generated by three source-detector pairs at separations of 3, 9, and 28 mm are illustrated in FIG. 5*a*. The reflected intensity is displayed on the y-axis while the yeast concentration (g/L) is displayed on the x-axis.

As can be seem from the source-detector pair having a 3 mm separation (triangles in FIG. 5*a*), there are 3 distinct regions of the reflectance curve. The reflectance at low concentrations (0.1-1 g/L) increases monotonically but with a weak dependence on concentration. At intermediate concentrations (5-50 g/L) the relationship between reflectance and concentration is linear. In the highest concentration range (>100 g/L), the reflectance curve becomes non-linear as it rolls off with increasing yeast concentration.

Examination of the source-detector pair with a 9 mm separation (squares in FIG. 5*a*) shows that the reflectance curve contains the same three distinct regions as with the emitter-detector pair separated by 3 mm. However, the entire curve has shifted to lower concentrations. In particular, it should be noted that the linear region of reflectance has shifted from approximately 5-50 to approximately 2-20. Similarly, for the 28 mm emitter-detector pair (circles in FIG. 5*a*), the linear region of reflectance is in range of 0.1-2 g/L. By multiplying each reflectance curve by a scalar multiplication factor (see above), the linear regions of the reflectance curves can be matched up to form a single continuous line (see FIG. 5*b*). The scalar factors applied were 1, 1.585, and 3.981 for the 3, 9, and 28 mm source-detector pairs, respectively. In commercial practice, these scaling factors could be determined during manufacture, stored in electronic memory, and then applied during measurement of samples by a user.

At any given concentration, the output reported by the sensor is simply the reading from the source-detector pair closest to the center of its linear range, multiplied by its scaling/multiplying factor (or equivalently offset after applying a logarithm). One method of arbitration is diagrammed in FIG. 11a. The logarithm of the signal measured from the first detector (d1) is added to an offset (C1) to produce a value (S1) which is compared to a pre-determined level (L1). If S1 is greater than L1, then the output result is equal to S1. If S1 is less than or equal to L1 then a second value (S2) is determined from the logarithm of the signal measured from the second detector (d2) plus a second constant (C2). If S2 is larger than a second pre-determined level (L2), then the output result is equal to S2. If S2 is less than or equal to L2 then a third value (S3) is computed by combining the logarithm of the signal measured by d3 to a third constant, and setting the output result equal to S3.

Figure 11B:
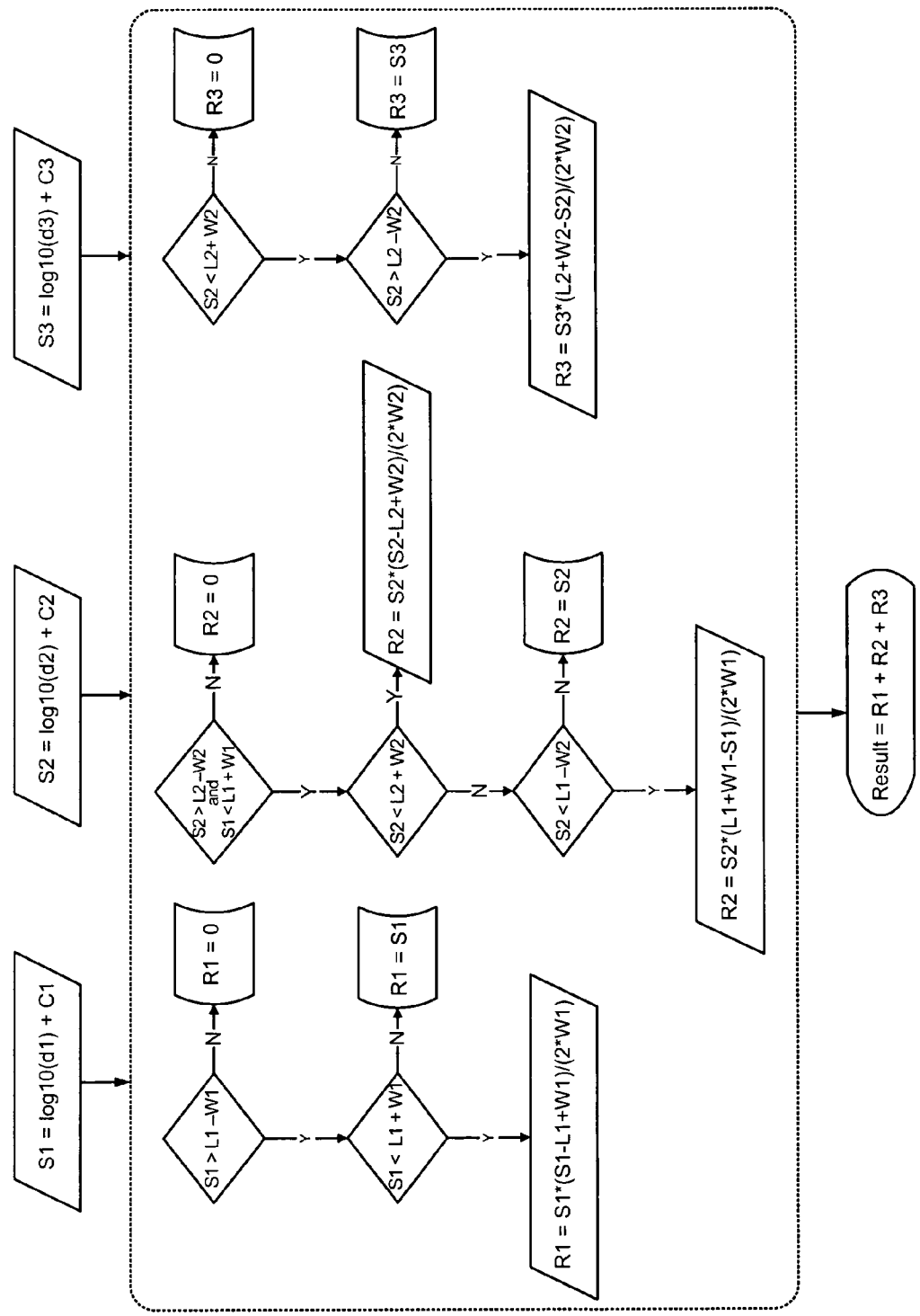
FIG. 11b presents a flow diagram summarizing an algorithm for arbitrating between three source-detector signals to produce a single output including a method of achieving a smooth transition between the source-detector pairs.

An alternative method of arbitrating between the source-detector pairs is diagrammed in FIG. 11b. This method provides a linear transition between the source-detector signals where the widths of these transitions (w1 and w2) are variables. Referring to the left side of FIG. 11b, the signal processed from detector (S1) does not contribute to the output result unless S1 is greater than a pre-determined level (L1) minus the width of the transition between detectors 1 and 2 (w1). If S1 is also less than the pre-determined level plus the transition width, then S1 is linearly weighted according to its value relative to the transition point; otherwise S1 contributes directly to the output result. The contributions of detectors 2 and 3 to the output result are similarly computed (as shown in the center and right of FIG. 11b), with the added complication for detector 2, that 2 transitions must be accounted for.

After combining the multiple source-detector signals into a single result according to one of the above algorithms, a table can be used interpolate the sensor result into a biomass. The table contains pair-wise values of sensor results (e.g., 25 pairs, 50 pairs, etc.) and logarithms of biomass. The current sensor result is compared to the table, and values bracketing the current sensor result are identified. The current sensor result is then linearly interpolated into the logarithm of biomass. An anti-log is applied to this result, to produce a biomass value.

Figure 5C:
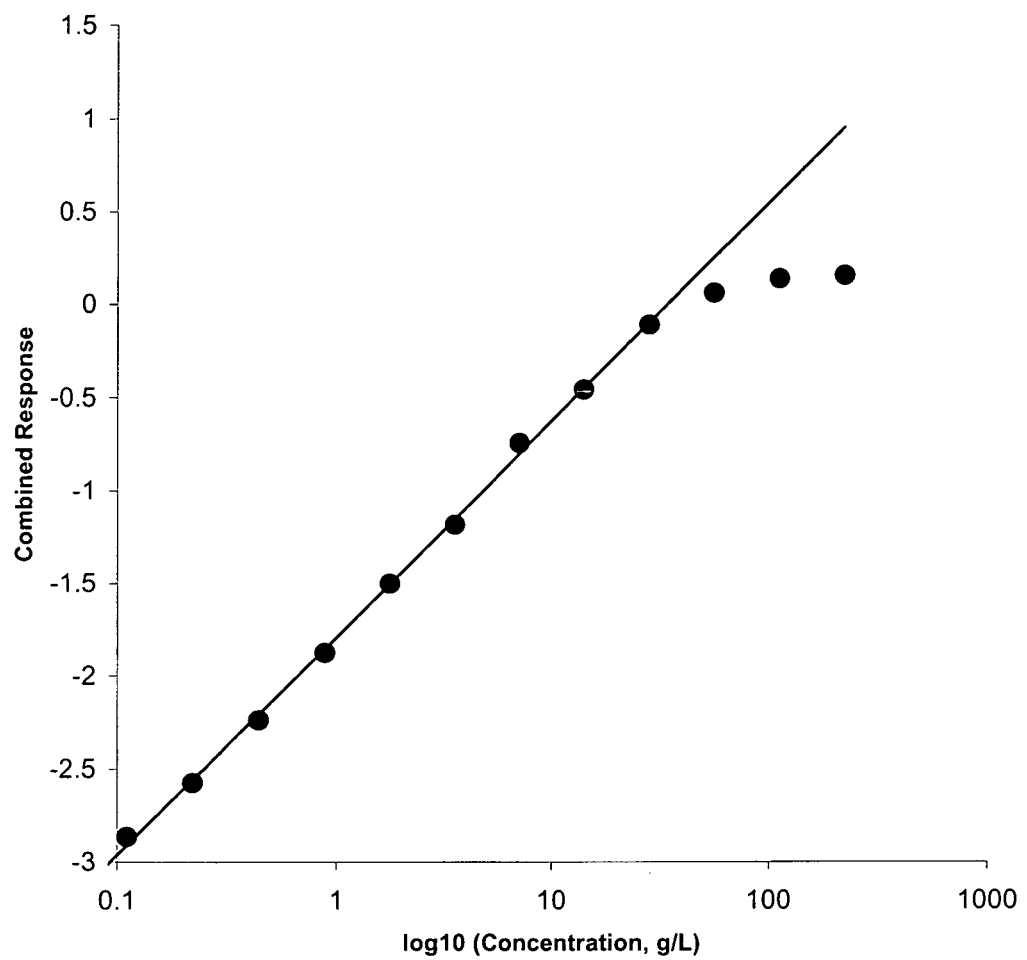
FIG. 5c presents a graph of the response from the same three source-detector pairs as in FIGS. 5a and b, combined according to an algorithm of an embodiment of the present invention.

In the current example, the algorithm is applied to three source-detector pairs spaced at 3, 6, and 18 mm. However, by analogy this algorithm can be easily reduced to apply to only two source-detector pairs or augmented to apply to additional source-detector pairs. For example, by applying the above algorithm to four source-detector pairs spanning separations of 6 to 28 mm, the combined response shown in FIG. 5c was generated. Notice that whereas each of the individual source-detector pairs on its own has a linear range of response spanning only about 1 order of magnitude (FIG. 5a), the combined response has a linear range of response that spans almost 3 orders of magnitude (FIG. 5c). The linear range may readily be extended further by the use of additional source-detector spacings; shorter-spaced emitter-detector pairs will extend the range of linearity at high concentrations while farther-spaced emitter-detector pairs will extend the range of linearity at low concentrations.

Reduced Sensitivity to Window Thickness

Figure 6A:
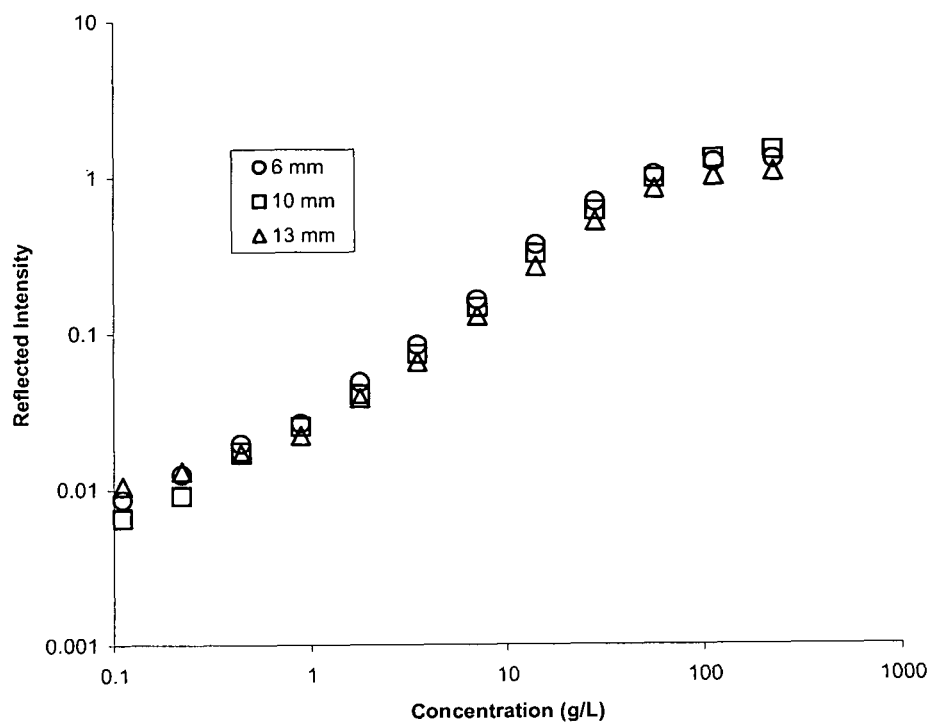
FIG. 6a presents a graph of the response generated by a source-detector pair separated by 6 mm, mounted to the exterior of three different vessels each with a different window thickness (6, 10, and 13 mm).
Figure 6B:
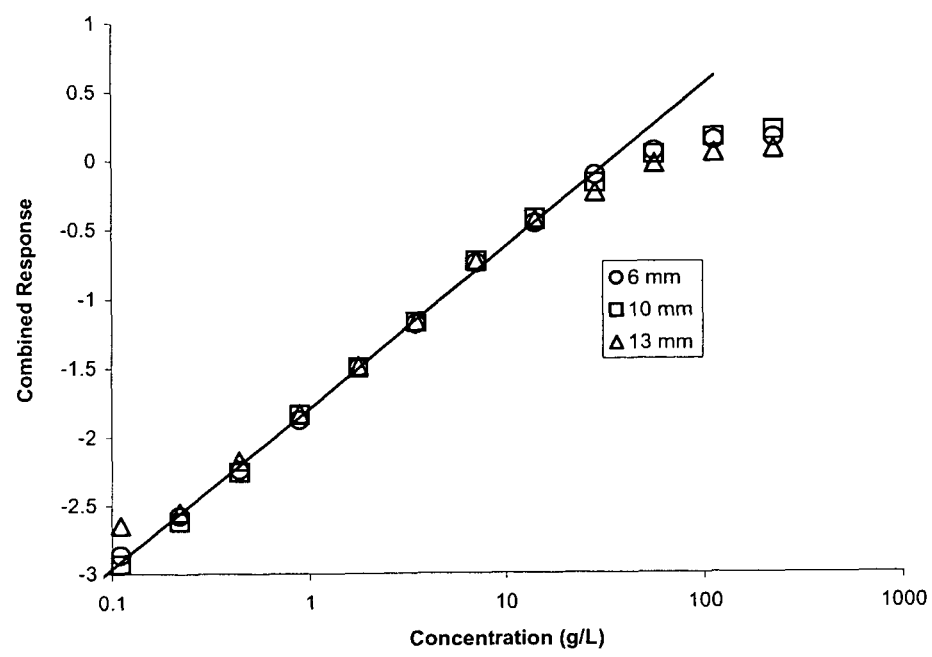
FIG. 6b presents a graph of the response from three source-detector pairs, combined according to an algorithm of an embodiment of the present invention, mounted to the exterior of three different vessels each with a different window thickness (6, 10, and 13 mm).

In addition to the benefit of wide linear response to particulate concentration, the present invention also confers the unanticipated benefit of reduced sensitivity to window thickness. FIG. 6a shows the experimentally measured reflectance measured by a single emitter-detector pair spaced 6 mm apart, when applied to vessels having 3 different window thicknesses (6, 10, and 13 mm). The signals measured through the 3 window thicknesses are different enough from each other that some method of compensation or calibration would be required to achieve accurate predictions of concentration. However, as shown in FIG. 6b, using the algorithm above to combine the response from multiple source-detector pairs results in a substantial decrease in sensitivity to window thickness. Over most of the concentration range, there is no significant dependence of the combined result on window thickness. At the highest concentrations, some dependence on window thickness is still observed. The data shown in FIG. 6a was collected without the benefit of an aperture placed in front of the detector. It is anticipated that by adding an aperture in front of the detector as described above and/or employing source-detector pairs with short separation, the sensitivity of the combined result to window thickness may be further reduced in the high concentration range.

Biomass Sensor with Reduced Sensitivity to Environmental Variables

Figure 7:
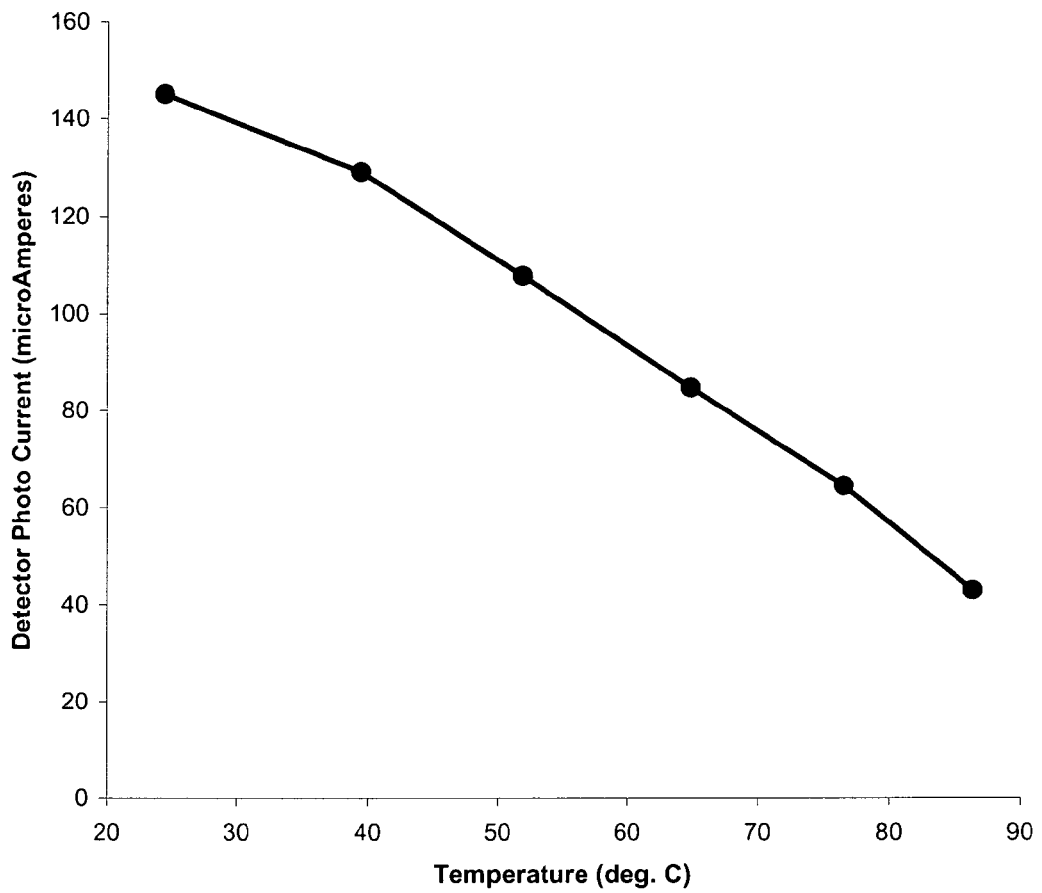
FIG. 7 presents a graph of the output detected from a diode laser as a function of temperature.
Figure 17:
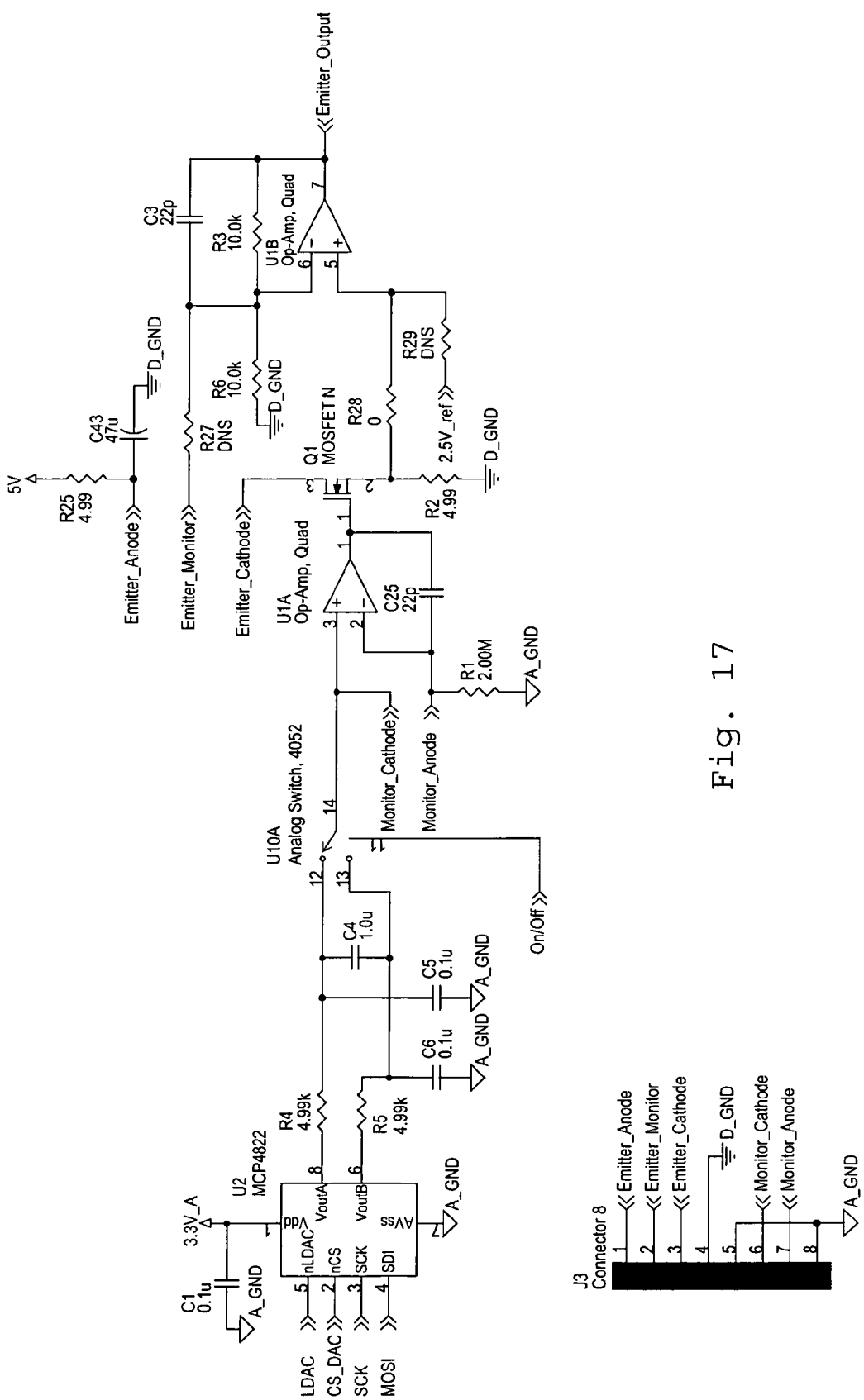
FIG. 17 shows an electronic schematic for controlling a laser source at a constant output power level in the presence of changing environmental influences such as changes in ambient light and temperature.

An example of the implementation of some of the above-described methods for compensating environmental variables is shown in the current example. The optical configuration of this embodiment was described above in the specification in description of to FIGS. 1-4. The effect of temperature variation on the output of an uncompensated laser is shown in FIG. 7. The laser is a surface-emitting laser diode being driven with approximately 25 mA of current and emitting approximately 5 mW of optical power at 850 nm. When operated at constant current the laser output intensity measured on a photodiode varies widely as a function of temperature. In the present example, a portion of the laser beam was directed towards a photodiode to monitor the laser output. The response of the photodiode was used as a feed-back control to maintain constant laser output despite changing temperature. An example of an electrical schematic for accomplishing this is shown in FIG. 17. The monitor anode and cathode are connected to the inputs of an operational amplifier U1A. The operational amplifier U1A is operated in feed-back mode to maintain a constant signal level on the photodiode. The signal level setting can be adjusted using a digital potentiometer U2. A transistor Q1 controlled by the output of the operation amplifier U1A is used to drive the laser.

In addition to compensating for changes in laser output power with temperature, the monitor photodiode can also compensate for changes in the sensitivity of the detectors due to temperature changes. This is accomplished by choosing a monitoring photodiode (e.g., 1572 as in FIG. 15) that has similar temperature sensitivity to the sensing detectors (e.g., 130, 132, and 134 in FIG. 1). When the temperature is changed and the sensitivity of the photodiodes is reduced, the emitter is driven harder to maintain a constant output of the monitor diode, compensating for the reduced sensitivity of the detectors.

The monitor diode also compensates for other difficult to control characteristics of a laser, such as mode hopping. Mode hopping is a relatively common occurrence in laser diodes in which small changes in current can lead to discontinuous changes in laser output power. When the laser starts oscillating between two adjacent modes, the instantaneous power will be varying, but the average output power of the laser is constant. In an example embodiment, the response time of the laser control loop is designed to be fast relative to the response time of an analog filter which is used to process the signal before it is converted from analog to digital form.

Using the beam splitter effectively provides a fixed reference for the magnitude of the amount of light reflected back to the detectors. In an alternative embodiment, rather than holding the laser output power fixed, the amount of light reflected back to the monitor diode by the beam splitter is divided into the relative amount of light reflected back to the other sensing photodiodes.

In one embodiment the laser is modulated between two closely spaced power levels. Detector feedback is used to set the output of both the low and high modulation levels. The advantage of this method is that ambient light reaching the feedback detector will affect the low and high modulation levels in the same manner, so that the difference between the low and high laser power levels will remain fixed despite stray light contamination.

Additional Embodiments

Figure 8A:
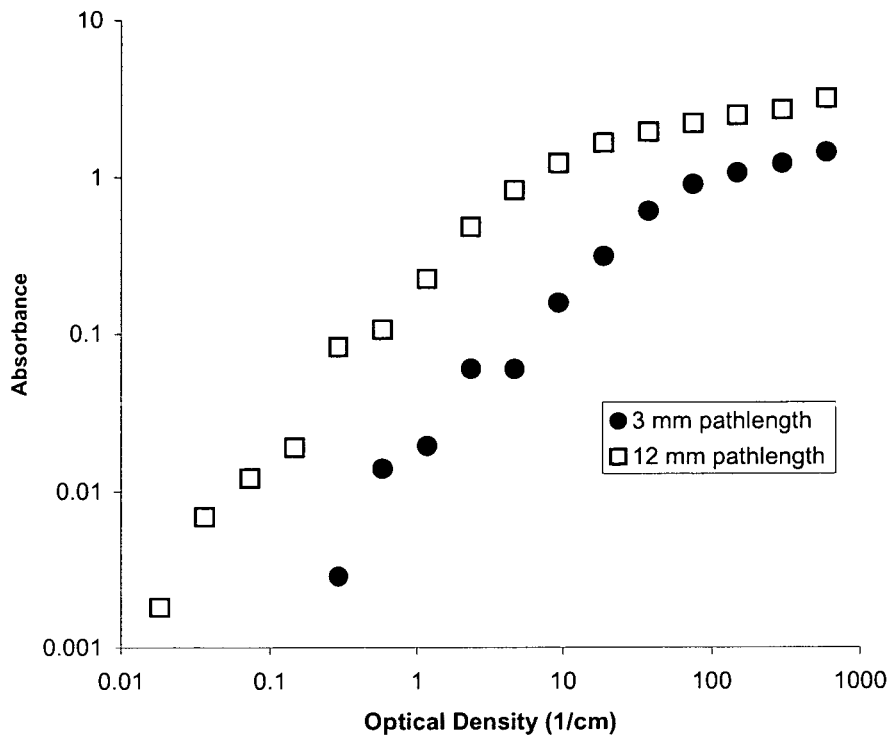
FIG. 8a presents a graph of the response of two source-detector pairs at two different separation distances measuring transmission through yeast in a bioreactor.
Figure 8B:
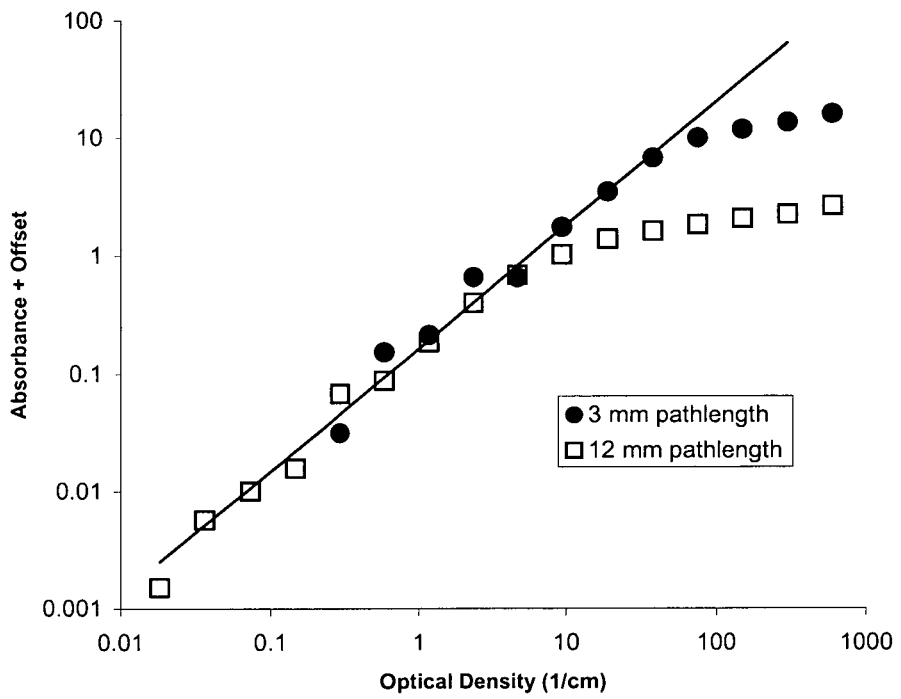
FIG. 8b presents a graph containing the same data as in 8a except the response of the source-detector pair separated by 3 mm has been offset according to an algorithm of an embodiment of the present invention.

Although the detailed description primarily focuses on reflectance measurements, the invention can also be used to extend the linear range of transmission measurements. To illustrate this point, transmission measurements through two path lengths, 3 and 12 mm, were performed in yeast suspensions. The resulting absorbance measured as a function of off-line optical density is shown in FIG. 8a. As with the reflectance measurements, by adjusting for offset, the linear range of sensitivity to biomass can be extended by the use of more than one source-detector pair (FIG. 8b). Through the use of additional source-detector pairs the linear range of sensitivity may be extended even further.

While the foregoing invention has been described in some detail for purposes of clarity and understanding, it will be clear to one skilled in the art from a reading of this disclosure that various changes in form and detail can be made without departing from the true scope of the invention. For example, all the techniques and apparatus described above can be used in various combinations. All publications, patents, patent applications, and/or other documents cited in this application are incorporated by reference in their entirety for all purposes to the same extent as if each individual publication, patent, patent application, and/or other document were individually indicated to be incorporated by reference for all purposes.

What is claimed is:

1. A method of determining concentration of at least one type of particle in a medium, the method comprising:
   (a) passing radiation from at least one source through said medium to at least one detector;
   (b) Measuring a plurality of signals corresponding to a portion of scattered radiation detected by at least one of said detectors;
   (c) comparing two or more of the signals for linearity and selecting one of the signals having highest linearity with respect to changes in a function dependent on particle concentration at the particle concentration currently being measured;
   (d) relating the at least one of the selected signals having highest linearity to the concentration of the at least one type of particle.

2. A method of determining concentration of at least one type of particle in a medium, the method comprising:
   (a) passing radiation originating from at least one source through said medium to at least one detector;
   (b) measuring a plurality of signals corresponding to the portion of scattered radiation detected by each of said detectors that originated from each of said sources;
   (c) selecting signals from a group comprising all of said signals, and combining the selected signals in a manner that results in highest weighting being given to the signal with highest linearity with respect to changes in a function dependent on particle concentration at the particle concentration currently being measured; wherein the selection of signals and said combining of the selected signals is carried out at least once, whereby at least one said combined result is produced and,
   (d) relating the at least one of the selected signals having highest linearity to the concentration of the at least one type of particle.

3. The method of claim 1, wherein sensitivity of the at least one detector to radiation scattered from outside of a defined volume within the medium is reduced by one or more of: passing of a beam of radiation reflected or transmitted from the defined volume in the medium through an aperture; using a lens in front of an aperture in front of a detector; and using an aperture whose length is substantially greater than its width and is made of material that is substantially absorbing of the radiation emitted by said source.

4. The method of claim 1, wherein sensitivity to variations in temperature of determining concentration is reduced by use of a feedback monitor, which monitor measures and maintains radiation output from the at least one radiation source.

5. The method of claim 1, wherein sensitivity to variations in ambient radiation of determining concentration is reduced by one or more of: placing a material between the medium and the at least one detector, which material diminishes the ambient radiation capable of reaching the at least one detector; and modulating the light source and detecting the radiation synchronously with the modulation.

6. The method of claim 1, wherein concentration determined indicates a biomass present in the medium.

7. The method of claim 1, wherein passing radiation comprises positioning a sensor externally to a container that holds said medium, said container providing a window into said medium that is substantially transparent to the radiation emitted by said sources.

8. The method of claim 1, wherein passing radiation comprises immersing a probe into the medium.

9. The method of claim 1, wherein passing radiation comprises wherein at least one of the plurality of signals measured by the at least one detector is transmitted via a mirror.

10. The method of claim 1, wherein the method is performed by a sensor held within an outershell, which outershell supports the sensor during attachment to a vessel comprising the medium, wherein the outershell comprises stackable elements.

11. The method of claim 1, wherein each of the plurality of signals is subjected to a mathematical manipulation; which manipulation is based on a prior calibration as separately determined for each source/detector pair that is manufactured.

12. The method of claim 1 or 2, wherein a particle-specific mathematical calibration is stored and applied to each concentration determination, which particle-specific calibration increases the accuracy of the concentration determination for a particular particle type.

13. The method of claim 1, wherein the radiation is back scattered to the one or more detectors.

14. The method of claim 1, wherein the radiation is passed from two or more sources to the one or more detectors, or wherein the one or more sources passes to two or more detectors.

15. The method of claim 1, further comprising combining two or more signals to provide a wider linear range than for one of the signals.

16. The method of claim 1, further comprising passing the radiation through a long narrow aperture.

17. The method of claim 7, wherein the measurement of particle concentration is initiated by physical contact between said sensor and said window.

18. The method of claim 7, further comprising contacting the window with the sensor, wherein orientation of said sensor upon contact with the window is made substantially parallel with the face of the window in at least one dimension.

19. The method of claim 7, wherein the sensor comprises a display of the concentration of the at least one type of particle and/or of a value related to the concentration.

20. The method of claim 7, wherein the sensor stores at least one value related to said particle concentration.

21. The method of claim 8, wherein said probe is integral to a disposable bioreactor.

22. The method of claim 8, wherein said probe comprises a fiber optic connector.

23. The method of claim 10, wherein the stackable elements are magnetically linked.

24. The method of claim 11, wherein the manipulation is done before said selecting.

25. The method of claim 11, wherein the manipulation is done after said selecting.

26. The method of claim 11, wherein the manipulation comprises an offset and/or a multiplication factor.

27. The method of claim 2, wherein sensitivity of the at least one detector to radiation scattered from outside of a defined volume within the medium is reduced by one or more of: overlapping of a beam of radiation from the at least one source and a beam of radiation reflected or transmitted from the defined volume within the medium to the at least one detector; passing of a beam of radiation reflected or transmitted from the defined volume in the medium through an aperture; focusing the radiation from said source so that the radiation beam is minimized within said defined volume; using a lens in front of an aperture in front of a detector; and using an aperture whose length is substantially greater than its width and is made of material that is substantially absorbing of the radiation emitted by said source.

28. The method of claim 2, wherein sensitivity to variations in temperature of determining concentration is reduced by use of a feedback monitor, which monitor measures and maintains radiation output from the at least one radiation source.

29. The method of claim 2, wherein sensitivity to variations in ambient radiation of determining concentration is reduced by one or more of: placing a material between the medium and the at least one detector, which material diminishes the ambient radiation capable of reaching the at least one detector; and modulating the light source and detecting the radiation synchronously with the modulation.

30. The method of claim 2, wherein concentration determined indicates a biomass present in the medium.

31. The method of claim 2, wherein passing radiation comprises positioning a sensor externally to a container that holds said medium, said container providing a window into said medium that is substantially transparent to the radiation emitted by said sources.

32. The method of claim 2, wherein passing radiation comprises immersing a probe into the medium.

33. The method of claim 2, wherein passing radiation comprises wherein at least one of the plurality of signals measured by the at least one detector is transmitted via a mirror.

34. The method of claim 2, wherein the method is performed by a sensor held within an outer shell, which outer shell supports the sensor during attachment to a vessel comprising the medium, wherein the outer shell comprises stackable elements.

35. The method of claim 2, wherein each of the plurality of signals is subjected to a mathematical manipulation; which manipulation is based on a prior calibration as separately determined for each source/detector pair that is manufactured.

36. The method of claim 1 or 2, wherein the concentration of the at least one type of particle is done for at least two time points; thereby determining a rate of change of concentration of the at least one type of particle.

37. The method of claim 31, wherein the measurement of particle concentration is initiated by physical contact between said sensor and said window.

38. The method of claim 31, further comprising contacting the window with the sensor, wherein orientation of said sensor upon contact with the window is made substantially parallel with the face of the window in at least one dimension.

39. The method of claim 31, wherein the sensor comprises a display of the concentration of the at least one type of particle and/or of a value related to the concentration.

40. The method of claim 31, wherein the sensor stores at least one value related to said particle concentration.

41. The method of claim 32, wherein said probe is integral to a disposable bioreactor.

42. The method of claim 32, wherein said probe comprises a fiber optic connector.

43. The method of claim 34, wherein the stackable elements are magnetically linked.

44. The method of claim 35, wherein the manipulation is done before said selecting.

45. The method of claim 35, wherein the manipulation is done after said selecting.

46. The method of claim 35, wherein the manipulation comprises an offset and/or a multiplication factor.

47. The method of claim 36, wherein the rate of change of concentration indicates the growth rate of organisms in the medium.

* * * * *

UNITED STATES PATENT AND TRADEMARK OFFICE
CERTIFICATE OF CORRECTION

PATENT NO. : 8,603,772 B2  
APPLICATION NO. : 12/220897  
DATED : December 10, 2013  
INVENTOR(S) : Martin P. Debreczeny Page 1 of 1

It is certified that error appears in the above-identified patent and that said Letters Patent is hereby corrected as shown below:

On the Title Page, (73) the Assignee should read:

BugLab LLC, Concord, CA (US)

Signed and Sealed this
Eleventh Day of November, 2014

Michelle K. Lee
*Deputy Director of the United States Patent and Trademark Office*